United States Patent
Hermansson et al.

(10) Patent No.: US 9,012,656 B2
(45) Date of Patent: Apr. 21, 2015

(54) OLIGOTHIOPHENE DERIVATE AS MOLECULAR PROBES

(75) Inventors: Ola Hermansson, Solna (SE); Peter Konradsson, Skanninge (SE); Andreas Aslund, Linkoping (SE); Shirin Ilkhanizadeh, Stockholm (SE); Rozalyn Simon, Linkoping (SE); Peter Nilsson, Linkoping (SE)

(73) Assignee: Celluminova AB, Norrköping (SE)

( * ) Notice: Subject to any disclaimer, the term of this patent is extended or adjusted under 35 U.S.C. 154(b) by 96 days.

(21) Appl. No.: 13/577,561

(22) PCT Filed: Feb. 15, 2011

(86) PCT No.: PCT/SE2011/050164
§ 371 (c)(1),
(2), (4) Date: Aug. 7, 2012

(87) PCT Pub. No.: WO2011/102789
PCT Pub. Date: Aug. 25, 2011

(65) Prior Publication Data

US 2012/0315646 A1    Dec. 13, 2012

Related U.S. Application Data

(60) Provisional application No. 61/304,820, filed on Feb. 16, 2010.

(30) Foreign Application Priority Data

Feb. 16, 2010 (SE) ....................................... 1050150

(51) Int. Cl.
*C07D 409/14* (2006.01)
*A61K 49/00* (2006.01)

(52) U.S. Cl.
CPC .......... *C07D 409/14* (2013.01); *A61K 49/0021* (2013.01); *A61K 49/006* (2013.01)

(58) Field of Classification Search
None
See application file for complete search history.

(56) References Cited

FOREIGN PATENT DOCUMENTS

| WO | 01/92877 A2 | 12/2001 |
| WO | 2006127712 | 11/2006 |

OTHER PUBLICATIONS

Chemical Abstract Registry No. 5660-45-7, indexed in the Registry File on STN CAS Online Nov. 16, 1984.*
Aslund, Andreas, et al., Novel pentameric thiophene derivatives for in vitro and in vivo optical imaging of a plethora of protein aggregates in cerebral amyloidoses, NIH Public Access, ACS Chem Biol.; Aug. 21, 2009; vol. 4(8): pp. 673-684.
Bjork, Per, et al., Conjugated polythiophene probes target lysosome-related acidic vacuoles in cultured primary cells, Molecular and Cellular Probes; 2007; vol. 21; pp. 329-337.
International Search Report for International Patent Application No. PCT/SE2011/050164, mailed May 13, 2011.
Extended European Search Report, corresponding to European Patent Application No. 11744969.4, issued by the European Patent Office, dated May 2, 2013.
Japanese Office Action, corresponding to Japanese Patent Application No. 2012-552839, issued by the Japanese Patent Office, dated Jun. 9, 2014.

* cited by examiner

*Primary Examiner* — Michael Barker
*Assistant Examiner* — Po-Chih Chen
(74) *Attorney, Agent, or Firm* — Michael G. Johnston; Moore & Van Allen PLLC

(57) ABSTRACT

The present invention relates to oligothiophene derivatives binding specifically to neural stem cells and neural cancer stem cells. More specifically, the invention relates to methods for detecting neural stem cells or neural cancer stem cells using said oligothiophene derivatives in a biological sample, as well as uses and kits relating thereto.

19 Claims, 2 Drawing Sheets

1A.

P1 (p-HTMI)

1B.

P2 (h-HTMI)

OLIGOTHIOPHENE DERIVATE AS MOLECULAR PROBES

CROSS-REFERENCE TO RELATED APPLICATIONS

This application is filed under the provisions of 35 U.S.C. §371 and claims the benefit of International Patent Application No. PCT/SE2011/050164, filed on Feb. 15, 2011, entitled "OLIGOTHIOPHENE DERIVATE AS MOLECULAR PROBES", which claims the benefit of priority of Swedish Application No. 1050150-0, filed on Feb. 16, 2010, and U.S. Provisional Application No. 61/304,820, filed on Feb. 16, 2010, the contents of all of which are hereby incorporated by reference herein in their entirety.

TECHNICAL FIELD

The present invention relates to novel oligothiophene derivates and their use as molecular probes. Particularly, the use of oligothiophene derivate as molecular probes as to detect, identify, separate and isolate neural stem cells is encompassed.

BACKGROUND OF THE INVENTION

Neurological conditions affect a large segment of the human population. With the percentage of people entering their elder years expected to increase in the next several decades, the percentage of people afflicted with a neurological condition is undoubtedly expected to increase as well.

One of the most prevalent neurological conditions is stroke, the leading cause of disability worldwide. Beyond the rehabilitation therapy following a stroke, once recovery from the stroke has reached a plateau and the neurological deficits are fixed, there are no accepted treatments to improve the neurological deficits.

Stem cells, such as neural stem cells, are normally identified, characterized and separated from other cells by immunohistological techniques, such as antibodies, targeting distinct biomolecular targets. However, these techniques are fraught with limitations—most markers as of today are not specific and selective enough to detect and identify neural stem cells in a complex biological system. Further, most existing markers require secondary methods for detection, which is time-consuming. It is also possible to mark selected cells genetically with, for example, a fluorescent protein such as GFP, but such marking requires genetic or invasive techniques and thus a modulation and most plausibly a selection of the cells.

Accordingly, the specific cells, e.g. the neural stem cells, are identified by several markers. Normally, an array, of suitable markers detectable by specific antibodies is used where some are more selective than others for the specific cell type analyzed. However it is the combined use of several markers that detects and identifies the cell type, e.g. the neural stem cell. Thus, each cell type, such as a neural stem cell, has a certain combination of markers on their surface that makes them distinguishable from other types of cells.

It is, however, time consuming and inefficient, and also less accurate, to use an array of less specific markers to detect and identify specific cell types such as neural stem cells. It is also difficult to use an array of antibodies for specific selection and isolation of neural cells, or, alternatively, use a purification method based on several sequential isolation steps using one marker each step. The latter may further prolong the isolation process causing a decrease in viability and quality of the isolated cells.

Thus, the development of molecules for selective and specific identification of single target molecules highly specific for neural stem cells is needed.

Molecules in which two or more thiophene rings linked together are named oligothiophenes. Such compounds possess interesting optical and electronic properties. Examples are fluorescence, semiconductance and light emission if correctly stimulated. One of the most outstanding properties of oligothiophenes is their fluorescence. By changing the structure it is possible to obtain emissions in the full visible spectrum.

Åslund et al reports a novel class of chemically defined oligothiophene derivate for the detection of pathogenic protein aggregates (Åslund et al., ACS Chem. Biol. 2009, 4, 673-684).

There is thus an urgent need to find more selective and specific markers for stem cells, particularly neural stem cells to detect and identify said cells, and to enable selective and specific isolation of said cells using a single target molecule instead of an array to improve viability and quality of the isolated cells. Accordingly, the present invention seeks to provide means and methods to allow such selective and specific detection, identification and isolation of neural stem cells.

SUMMARY OF THE INVENTION

One aspect of the present invention provides an oligothiophene derivate according to formula (I)

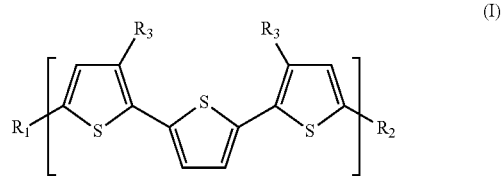

wherein
$R_3$ may be chosen from

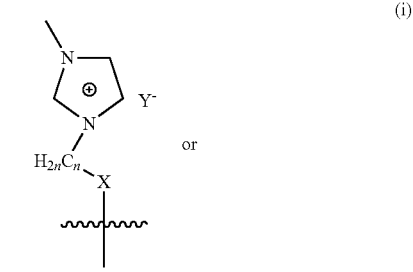

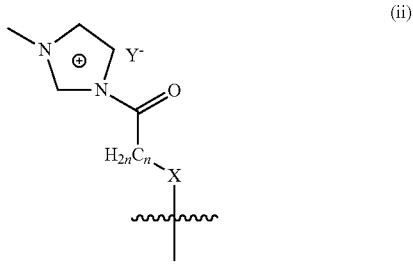

and wherein n vary from 0 to 3,

Y⁻ is the anionic counter ion and may be but is not limited to bromine, chlorine, iodine, 4-methylbenzenesulfonate or any other physiologically feasible anion, X can be chosen from O (n≥1, such as 1, 2, 3, etc.) or $CH_2$ (n=0-3), and each $R_1$ and $R_2$ is independently selected from 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8), methyl 2-yl-thiophene-5-carboxylate (9). Further, 5-fluorothiophene-2-yl (10) may have enriched isotopes of $^{18}F$ or $^{19}F$. For 5 the proton in the 5-position may be substituted with tritium (11) and for 4 the methyl group may consist of isotopically enriched carbon such as $^{11}C$ (12) (shown here below)

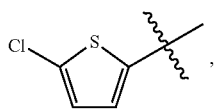
1

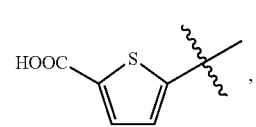
2

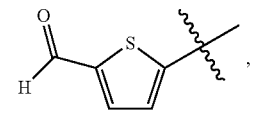
3

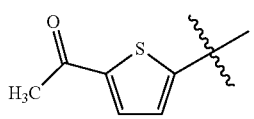
4

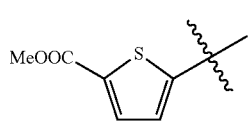
5

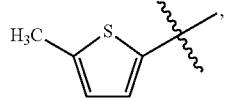
6

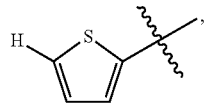
7

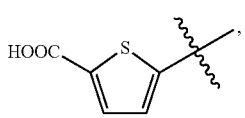
8

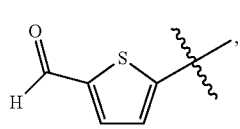
9

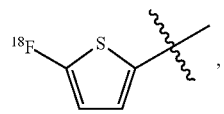
10

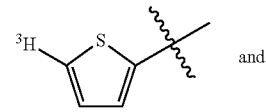
and
11

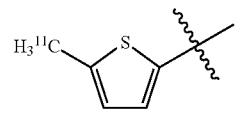
12

In another embodiment $R_1$ may be

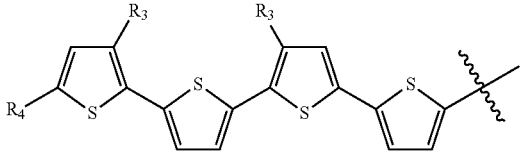
(iii)

wherein n vary from 0 to 3

Y⁻ is, as above in formula (I), the anionic counter ion and may be but is not limited to bromine, chlorine, iodine or 4-methylbenzenesulfonate, X can be chosen from O (n≥1) or $CH_2$ (n≥0), and $R_4$ is selected from bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl (10) with enriched isotopes of $^{18}F$ or $^{19}F$. Starting with 5 the proton in the 5-position may be substituted with tritium (11) and for 4 the methyl group may consist of isotopically enriched carbon such as $^{11}C$ (12).

-continued

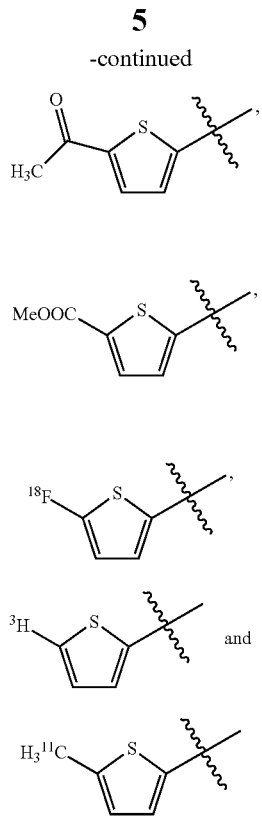

Further embodiments are wherein $R_1$ is according to formula (iii) then $R_2$ may be selected from bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12):

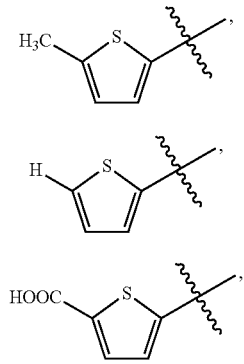

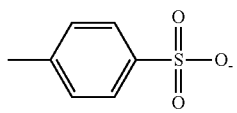

-continued

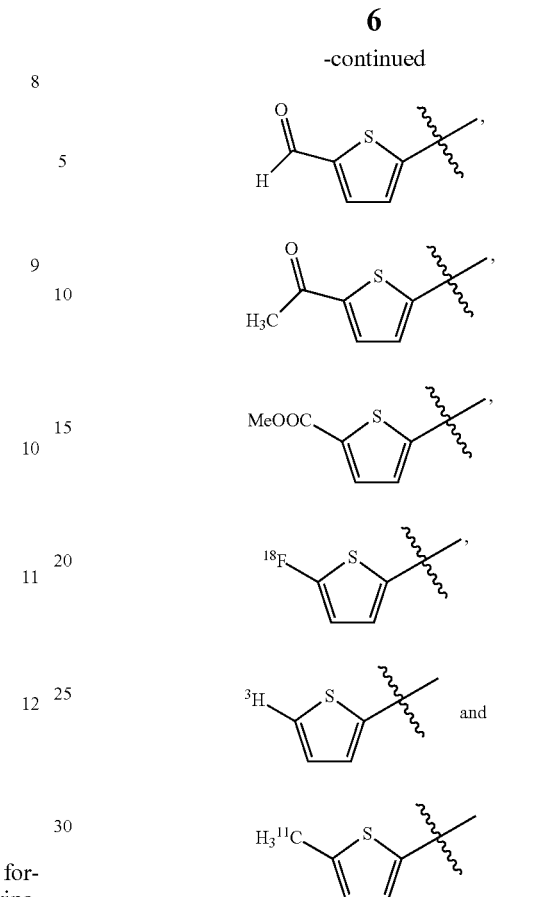

Further embodiments are wherein $R_3$ is according to formula (i), and wherein n is 1, X is $CH_2$, $Y^-$ is 4-methylbenzenesulfonate, and $R_1$ and $R_2$ is 5 according to formula

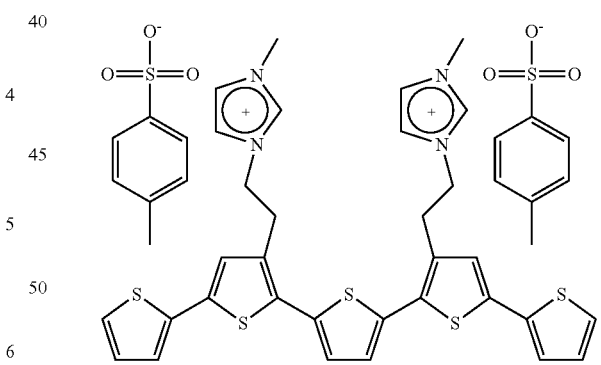

Further embodiments are wherein $R_3$ is according to formula (i), and wherein n is 1, X is $CH_2$, $Y^-$ is 4-methylbenzenesulfonate, $R_1$ is iii and $R_2$ is hydrogen according to formula

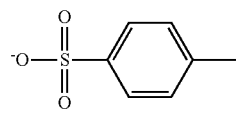

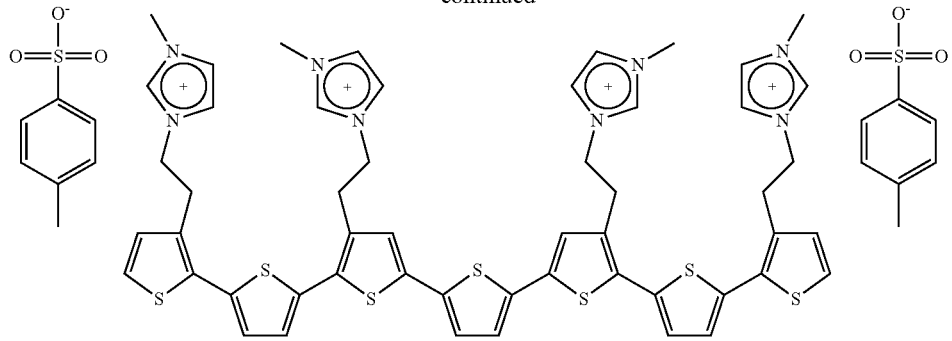

Further embodiments are wherein the oligothiophene derivatives according the invention are luminescent.

A further aspect of the present invention provides a composition for detecting neural stem cells and neural cancer stem cells comprising any of the oligothiophene derivatives according to the invention.

A further aspect of the present invention provides a method for detecting neural stem cells in a biological sample in vitro or in vivo, the method comprising the steps of
 a. contacting said sample with an oligothiophene derivate according to the invention or a composition comprising at least one oligothiophene derivate according to the invention or the composition according to the invention, for sufficient time to form at least one neural stem cell-oligothiophene derivate complex,
 b. detecting said neural stem cell-oligothiophene derivate complexes.

Further embodiments are wherein the amount of neural stem cell-oligothiophene derivate complexes detected are compared to a positive and/or negative control, thereby detecting the neural stem cells.

Further embodiments are wherein the neural stem cell is a neural cancer stem cell.

Further embodiments are wherein the positive control comprises neural stem cells or neural cancer stem cells or parts thereof.

Further embodiments are wherein the negative control does not comprise neural stem cell or neural cancer stem cells.

In further embodiments the method further comprises a step of optionally scoring the amount of neural stem cells-oligothiophene derivative complex or neural cancer stem cells-oligothiophene derivate complexes.

In further embodiments the method according to the invention is a method which is performed on an automated staining device.

In still further embodiments, the method is performed manually.

In still further embodiments the detection is made manually.

Further embodiments are wherein the detection is made by image analysis.

Still a further aspect of the invention provides a method for separating neural stem cell or neural cancer stem cells from other biological material in a biological sample, the method comprising the steps of
 a. contacting said sample with an oligothiophene derivate according to the invention or the composition according to the invention, for sufficient time to form at least one neural stem cell oligothiophene derivative complex or neural cancer stem cell-oligothiophene derivate complex,
 b. detecting said neural stem cell-oligothiophene derivate complexes or neural cancer stem cell-oligothiophene derivative complex,
 c. separating said detected complex, thereby separating neural stem cells or neural cancer stem cells.

Further embodiments are wherein the method further comprises the step of isolating said neural stem cells or neural cancer stem cell.

Further embodiments are wherein the isolation is done by mechanical means e.g. using beads, columns, panning etc.

Further embodiments are wherein the isolation is done by flow cytometric means such as e.g. FACS.

In all further aspects and embodiments, neural cancer stem cells are included as well as neural stem cells. Either together, if the biological sample comprises both types of cells, or separately, if the biological sample comprises only non-cancerous neural stem cells or neural cancer stem cells respectively.

Further aspects of the invention are uses of the oligothiophene derivatives according to the invention or the composition according to the invention, to detect neural stem cells in vitro or in vivo, Further aspects provides a kit comprising
 a. an oligothiophene derivatives according to the invention or a composition according to the invention, and
 b. optionally, instructions for using the oligothiophene derivate or the composition.

Further aspects of the invention provides a kit for detecting neural stem cells in vitro or in vivo, the kit comprising
 a. an oligothiophene derivate according to the invention or the composition according to the invention, and
 b. optionally, instructions for using the oligothiophene derivate or the composition.

Further aspects of the invention provides a kit for separating neural stem cells, the kit comprising
 a. an oligothiophene derivate according to the invention or the composition according to the invention, and
 b. optionally, instructions for using the oligothiophene derivate.

Further embodiments are wherein the kit according to the invention further comprises means to isolate said neural stem cells.

BRIEF DESCRIPTION OF DRAWINGS

FIG. 2A shows control, FIG. 2B shows staining with Compound 1 (not binding to neural stem cells or neural cancer stem cells), FIG. 2C shows binding of Compound 2 (p-HTMI) to neural stem cells. FIG. 2D shows staining of a mixture of Compound 1 and Compound 2 to neural stem cells, showing strong binding of compound 2 (right hand peak) to said cells. FIG. E overlay histograms of control and compound 1 (right hand peak in bold) and FIG. 2F shows overlay histograms of compound 2 (right hand peak in bold) and control.

DETAILED DESCRIPTION OF THE INVENTION

Definitions

Figure 1:
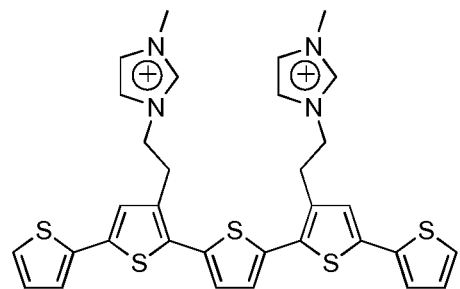
FIG. 1 depicts two embodiments of the invention in A) P1 (p-HTMI) and B) P2 (h-HTMI), respectively.
Figure 1:
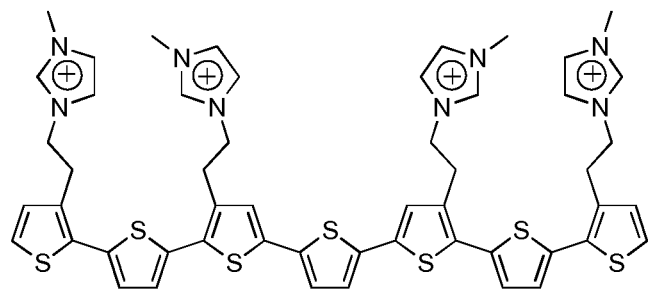

"Subject" as used herein denotes a mammal, such as a rodent, a feline, a canine, and a primate. Preferably a subject according to the invention is a human.

"At least one" as used herein means one or more, i.e. 1, 2, 3, 4, 5, 6, 7, 8, 9, 10 etc.

"Detection", "detect", "detecting" as used herein includes qualitative and/or quantitative detection (measuring levels) with or without reference to a control, and further refers to the identification of the presence, absence, or quantity of a given target, specifically the target of an oligothiophene derivate of the invention.

As used herein, the singular forms "a", "and", and "the" include plural referents unless the context clearly dictates otherwise. Thus, for example, reference to "an antibody" includes a plurality of such antibodies.

"Diagnosis" as used herein encompasses the identification of the nature of a disease.

"Prognosis" as used herein encompasses a forecast as to the probable outcome of a disease, the prospects as to recovery from a disease as indicated by the nature and symptoms of a disease.

"Sensitivity", as used herein in the context of its application to detecting neural stem cells in different assays or methods, refers to the proportion of all biological samples that are correctly identified as such.

"Specificity" of an assay or method, as used herein refers to the proportion of all biological samples that are correctly identified as such.

As used herein, "neural stem cells" refers to a type of stem cell that resides in the brain, which can make new nerve cells (called neurons) and other cells that support nerve cells (called glia). In the adult, neural stem cells can be found in very specific and very small areas of the brain where replacement of nerve cells is seen.

As used herein, "neural cancer stem cells" (neural CSC) or "neural cancer stem cell like cells" refers to a type of neural stem cells in a tumour that have the capability to self-renewal, and are characterized by uncontrolled, abnormal growth of said cells.

As used herein a "biological sample" or simply "sample" encompasses a variety of sample types obtained from any subject. Exemplary biological samples useful in the disclosed methods include but are not limited to biological samples disclosed herein such as e.g. solid tissue samples such as a biopsy specimen or tissue cultures or cells derived there from, and the progeny thereof. For example, biological samples include cells obtained from a tissue sample collected from an individual. Thus, biological samples encompass clinical samples, cells in culture, cell supernatants, cell lysates, and tissue samples, e.g. tissue samples from a brain such as an adult brain, tumour samples from the brain, etc.

Samples may be fresh or processed post-collection (e.g., for archiving purposes). In some examples, processed samples may be fixed (e.g., formalin-fixed) and/or wax- (e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, Histotechology: A Self-Instructional Text, Chicago:ASCP Press, 1997). In some examples, the sample (or a fraction thereof) is present on a solid support.

Solid supports useful in a disclosed method need only bear the biological sample and, optionally, but advantageously, permit convenient detection of the cells of interest in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)), beads or BIACORE®; chips.

The term "algorithm" as used herein refers to a mathematical formula that provides a relationship between two or more quantities. Such a formula may be linear, or non-linear, and may exist as various numerical weighting factors in computer memory.

By "reacting specifically with" as used herein it is intended to equal "capable of binding selectively" or "binding specifically to". As used herein the expressions are intended to mean that the oligothiophene derivatives according to the invention which is capable of binding to neural stem cell and further which binds at least 10-fold more strongly the neural stem cell than to another cells for example at least 50-fold more strongly or at least 100-fold more strongly. The oligothiophene derivate may be capable of binding selectively to the protein under physiological conditions, e.g. in vivo. Suitable methods for measuring relative binding strengths include using a competitive assay or BIACORE® analysis (Bioacore International AB, Sweden)

In the methods and uses disclosed where neural stem cells are detected and identified by oligothiophene derivate of the invention a scoring of the neural stem cells may optionally be used. The scoring may be semi-quantitative; for example, with binding of oligothiophene derivate to a neural stem cell forming a complex recorded as 0, 1, 2, 3 or 4 (including, in some instances plus (or minus) values at each level, e.g., 1+, 2+, 3+, 4+) with 0 being substantially no complex detectable 3 (or 4+) being the highest detected complex formation. In such methods, an increase or decrease in the corresponding complex formation is measured as a difference in the score as compared the applicable control (e.g. a standard value or a control sample); that is, a score of 4+ in a test sample as compared to a score of 0 for the control represents increased complex formation in the test sample, and a score of 0 in a test sample as compared to a score of 4+ for the control represents decreased complex formation in the test sample.

The development of molecules for selective and specific identification of neural stem cells have received increasing attention owing to their large potential for being used as analytic tools for a wide range of application within the field of molecular biology, medicine and biotechnology. Thus, discussed above, simpler and more sensitive specific markers for identifying neural stem cells are needed.

The present invention utilizes small synthetic molecular dyes being advantageous as such since the dyes can be chemically tailor made to selectivity identify stem cells by simpler and still highly sensitive and specific means and methods. The luminescent oligothiophene derivatives and methods using such dyes for specific identification of neural stem cells through distinct optical signals of the compounds as provided herein are highly appreciated.

As revealed above, the present invention provides means and methods for sensitive and selective detection, identification, separation and isolation of neural stem cells and neural cancer stem cells.

Neural cancer stem cells are found in neural cancer tissue. Example of neural cancer is glioma. A glioma is a type of tumour that starts in the brain or spine. It is called a glioma because it arises from glial cells. The most common site of gliomas is the brain.

Gliomas are named according to the specific type of cell they most closely resemble. The main types of gliomas are:
Ependymomas—ependymal cells
Astrocytomas—astrocytes—Glioblastoma multiforme is the most common astrocytoma.
Oligodendrogliomas—oligodendrocytes
Mixed gliomas, such as oligoastrocytomas, contain cells from different types of glia.

Gliomas are difficult to cure. Surgery is available for oligodendroglioma and grade I astrocytoma that are benign. The prognosis for patients with high-grade gliomas is generally poor, and is especially so for older patients. Of 10,000 Americans diagnosed each year with malignant gliomas, about half are alive 1 year after diagnosis, and 25% after two years. Those with anaplastic astrocytoma survive about three years. Glioblastoma multiforme has a worse prognosis with less than 12 month survival after diagnosis.

Treatment for brain gliomas depends on the location, the cell type and the grade of malignancy. Often, treatment is a combined approach, using surgery, radiation therapy, and chemotherapy. The radiation therapy is in the form of external beam radiation or the stereotactic approach using radiosurgery. Spinal cord tumours can be treated by surgery and radiation. Temozolomide is a chemotherapeutic drug that is able to cross the blood-brain barrier effectively and is being used in therapy.

More specifically, the invention provides oligothiophene derivatives binding specifically to neural stem cells. Said oligothiophene derivate is exposed to a sample comprising at least one neural stem cell whereby the oligothiophene derivate and the neural stem cell interacts, forming a complex, said complex being detectable as a change of luminescence of the oligothiophene derivate in response to binding on the neural stem cell. The detected change of luminescence is then in its further applications used to detect, identify, separate or isolate neural stem cells.

The present invention is thus based on the chemical properties of the molecule allowing a selective (specific) uptake by neural stem cells where the molecule becomes luminescent based on chemical and structural properties in the interactions with proteins within the neural stem cells.

The present invention is based on the chemical properties of the molecule allowing a selective (specific) uptake by neural stem cells where the molecule becomes luminescent based on chemical and structural properties in the interactions with proteins within the neural stem cells.

The interaction occurs without covalent bonding and is based on hydrogen bonding, electrostatic and non-polar interactions—herein after referred to as non-covalent bonding and which further includes any type of bonding that is not covalent in nature—between the oligothiophene derivate and the molecular motif on the neural stem cell.

The present invention utilizes interactions between an oligothiophene derivative and a neural stem cell specific molecular motif, which induce conformational restriction of the oligothiophene derivative. Furthermore, these conformational restrictions alter the optical properties of the oligothiophene derivative, leading to enhanced emission from oligothiophene derivative. Thus, neural stem cells are easily identified due to a distinct enhanced fluorescence from the oligothiophene derivative. Furthermore, said emission spectra from the oligothiophene derivative bound selectively to molecular target/s within the neural stem cells and not other cell types the neural stem cell specific molecular target can be utilized for detection, identification, separation or isolation of said stem cells.

Examples of oligothiophene derivatives exhibiting the above discussed characteristics are p-HTMI and h-HTMI (see FIG. 1a, formula P1, and b, formula P2) have proven useful for selective identification of neural stem cells, whereas similar previously reported conjugated polythiophenes and conjugated polyeelectrolytes are lacking this property (see e.g. (Äslund et al., ACS Chem. Biol. 2009, 4, 673-684). Hence, the distinct side chain functionalization of p-HTMI and h-HTMI is necessary for a selective interaction with the molecular target present in neural stem cells. The detailed description of the invention that follows will deal separately with the oligothiophene derivatives, stem cells and methods for detection, identification, separation or isolation of stem cells. The invention is finally exemplified with a number of experiments demonstrating the utility thereof.

Oligothiophene Derivatives

The present invention relates to a variety of oligothiophene derivatives, with a distinct numbers of monomers ranging from 5-10 mers, consisting of mers derived from thiophene or thiophene derivatives.

The oligothiophene derivatives are monodispersed, consist of thiophene chains with a well-define chain length.

Thus, said oligothiophene derivates according to the invention consist of one or more thiophene trimer units. The trimer unit consists of a thiophene with a substituent followed by an unsubstituted thiophene and, finally, another thiophene with a substituent follows.

The trimer building block may be used in various combinations, also with other thiophene derivatives.

Furthermore, monomers with anionic-, cationic or zwitterionic side chain functionalities are included in further embodiments, when the oligothiophene derivatives are conjugated by side chains. The side chain functionalities may be derived from, but not limited to, amino acids, amino acid derivatives, neurotransmittors, monosaccharides, nucleic acids, or combinations and chemically modified derivatives thereof.

In further embodiments, the above mentioned oligothiophenes are functionalized for a diversity of imaging setups, including magnetic resonance imaging (MRI), emission positron resonance imaging (EPRI), positron emission tomography (PET) or multi-photon imaging.

Radionuclides used in PET scanning are typically isotopes with short half lives such as carbon-11 (~20 min), nitrogen-13 (~10 min), oxygen-15 (~2 min), and fluorine-18 (~110 min). These radionuclides are incorporated in the oligothiophene derivatives according to the invention that bind to neural stem cells or neural cancer stem cells. Such labeled compounds are known as radiotracers. Due to the short half lives of most radioisotopes, the radiotracers must be produced using cyclotron and radiochemistry laboratories that are in close proximity to the PET imaging facility. The half-life of fluorine-18 is long enough such that fluorine-18 labeled radiotracers may be manufactured commercially at an offsite location.

Thus, further embodiments are wherein the side chain functionalities are e.g. amino acids, amino acid derivatives, neurotransmittors, monosaccharides, nucleic acids, or combinations and chemically modified derivatives thereof.

The conjugated oligothiophene derivatives of the present invention may contain a single side chain functionality or may comprise two or more different side chain functionalities. Thus, further embodiments are wherein the oligothiophene derivatives of the present invention are conjugated with side chains and wherein the side chains comprise a single side chain functionality or comprise two or more different side chain functionalities.

Examples, however, with no limitations to other apparent to any one skilled in the art of oligothiophene derivate and of conjugations, functionalities etc., are given herein.

Thus, one aspect of the present invention provides an oligothiophene derivate according to formula (I)

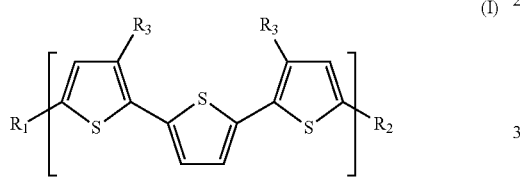

wherein
$R_3$ may be chosen from

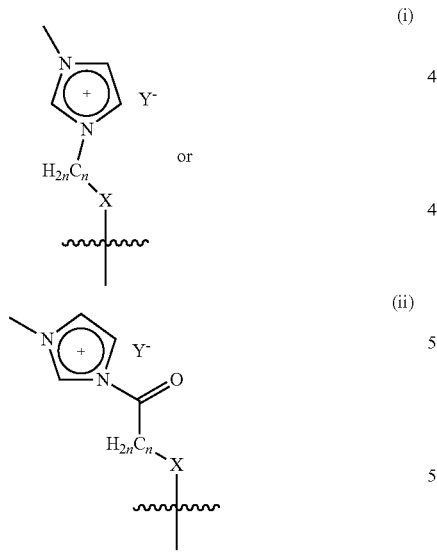

and wherein
n may vary from 0 to 3,
$Y^-$ is the anionic counter ion and may be but is not limited to bromine, chlorine, iodine or 4-methylbenzenesulfonate,
X may be chosen from O (n≥1) or $CH_2$ (n=0-3), and
each $R_1$ and $R_2$ is independently selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9)), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) shown below:

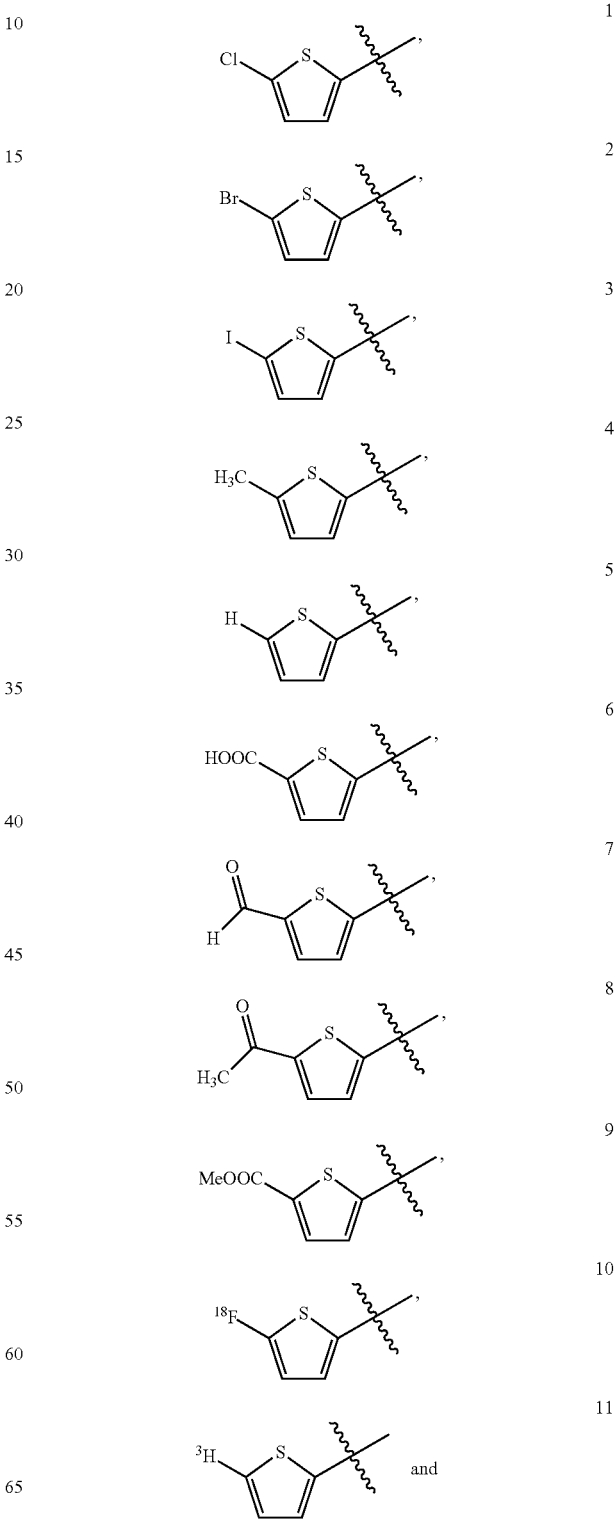

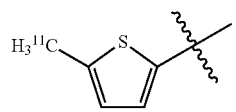

In another embodiment $R_1$ may be

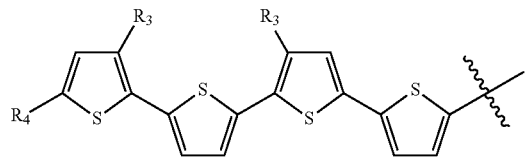
(iii)

and when $R_1$ is (iii), n may vary from 0 to 3, $Y^-$ is the anionic counter ion and may be but is not limited to bromine, chloride, iodine or 4-methylbenzenesulfonate, and X may be chosen from O (n≥1) or $CH_2$ (n≥0) and $R_4$ is selected from bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) shown below:

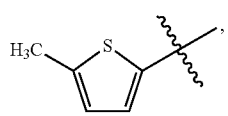
4

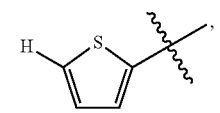
5

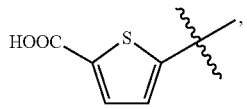
6

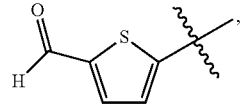
7

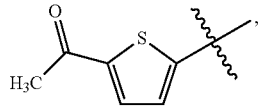
8

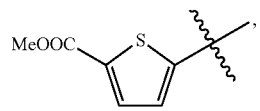
9

In further embodiments, if $R_1$ is formula (iii) then $R_2$ may be selected from bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) shown in the formulas below:

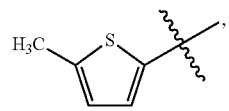
4

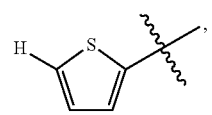
5

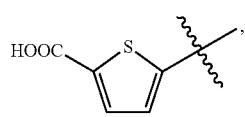
6

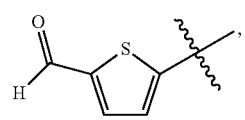
7

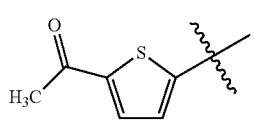
8

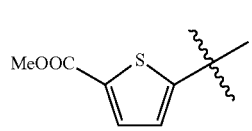
9

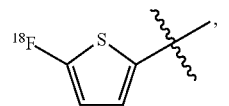
10

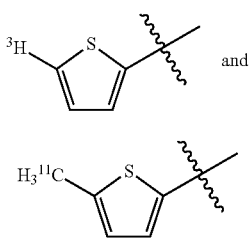

Further embodiments are wherein $R_3$ is according to formula (i), and wherein n is 1, X is $CH_2$, $Y^-$ is 4-methylbenzenesulfonate, $R_1$ and $R_2$ is according to formula 5 which will give formula

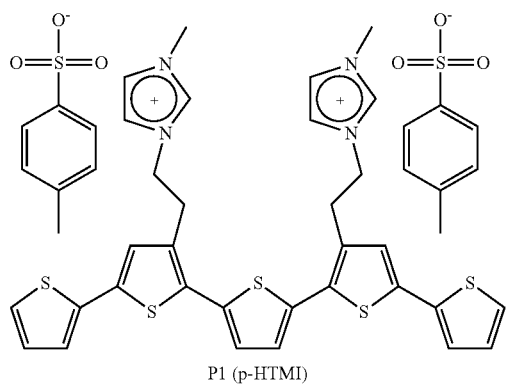

P1 (p-HTMI)

Still further embodiments are wherein $R_3$ is (I), n is 1, X is $CH_2$, $Y^-$ is 4-methylbenzenesulfonate, $R_1$ is (iii) and $R_2$ is hydrogen according to formula

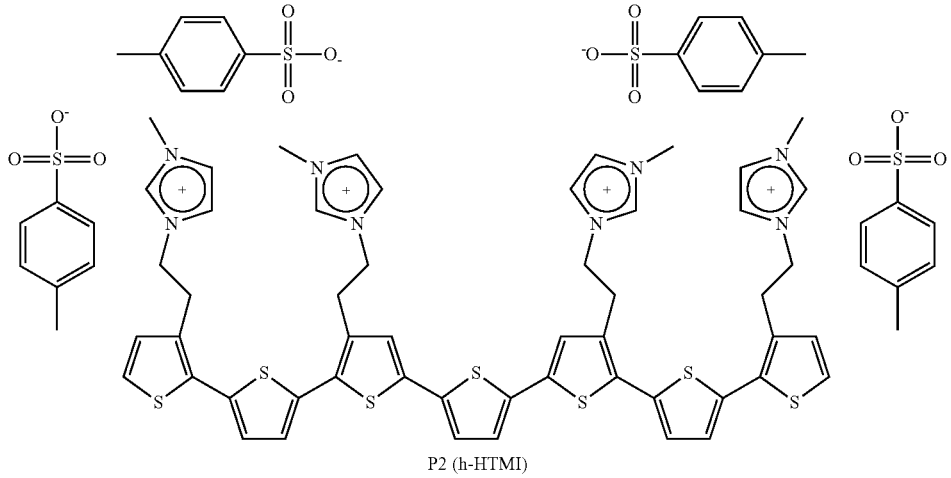

P2 (h-HTMI)

All pharmaceutically acceptable salts of the oligothiophene derivatives of the present invention are, of course, also encompassed.

The oligothiophene derivatives according to the invention may also be luminescent. Thus, further embodiments are wherein the oligothiophene derivatives according the invention are luminescent.

The oligothiophene derivatives may also be conjugated to provide certain functionalities to said oligothiophene derivatives. Further embodiments are thus wherein the oligothiophene derivatives are conjugated with side chains that may provide the oligothiophene derivative with certain functions.

Examples are e.g. modifications by the covalent attachment of polyethylene glycol or other suitable polymer, and uses of the same.

A further example of modifications by covalent attachment is attachment of a nano particle, normally sized <100 nm in diameter, to the oligothiophene derivatives of the invention.

Further provided herein is that the oligothiophene derivatives according to the invention may be labelled directly or indirectly, with a detectable moiety. By directly labelled is meant that the detectable moiety is attached to the oligothiophene derivative. By indirect labelled it is meant that the detectable moiety is attached to a linker, such as, for example, a secondary or tertiary antibody. The detectable moiety may be any moiety or marker known to those skilled in the art, or as described herein, and as being such a moiety being capable of generating a signal that allows the direct or indirect quantitative or relative measurement of a molecule to which it is attached.

A wide variety of detectable moieties, or labels, and conjugation techniques are known and reported extensively in both the scientific and patent literature. Suitable labels include radionuclides, enzymes, substrates, cofactors, inhibitors, fluorescent agents, chemiluminescent agents, magnetic particles and the like.

The detectable moiety may be a single atom or molecule, which is either directly or indirectly involved in the production of a detectable species. Optionally, the detectable moiety is selected from the group consisting of a fluorescent moiety, an enzyme linked moiety, a biotinylated moiety and a radiolabeled moiety, as described further herein, e.g. below. By "label", "detectable moiety" is meant any detectable tag that can be attached directly (e.g., a fluorescent molecule integrated into an oligothiophene derivative) or indirectly (e.g., by way of binding to a primary oligothiophene derivative with a secondary, tertiary or further reagent, such as e.g. an antibody with an integrated fluorescent molecule) to the molecule of interest. Thus, a label, marker or detectable moiety is any tag that can be visualized, for example, with imaging methods.

By a "detectable moiety" we further include the meaning that the moiety is one which, when located at the target motif site following providing the oligothiophene derivative of the invention or the composition of the invention to a biological sample, such as a tissue sample, e.g. a human brain tissue sample, may be detected in vitro or in vivo. That includes that the detectable moiety is signal generating and it is further convenient and thus included in further embodiments if the detectable moiety may be detected and the relative amount and/or location of the moiety (for example, the location on an tissue sample) may be determined. Detectable moieties are well known in the art.

Thus, the oligothiophene derivative or the composition of the invention is useful in methods further exemplified herein, e.g. by methods and uses for detection of neural stem cells in vitro or in vivo of biological samples. In further embodiments, image systems are used as exemplified further herein.

Suitable detectable moieties are well known in the art and the attachment or linking of these moieties to oligothiophene derivatives is further well known in the art. Further examples of detectable moieties are an enzyme; an enzyme substrate; an enzyme inhibitor; coenzyme; enzyme precursor; apoenzyme; fluorescent substance; pigment; chemiluminescent compound; luminescent substance; coloring substance; magnetic substance; or a metal particle such as gold colloid; a radioactive substance such as $^{125}I$, $^{131}I$, $^{32}P$, $^{3}H$, $^{35}S$, $^{18}F$, $^{11}C$ or $^{14}C$; a phosphorylated phenol derivative such as a nitrophenyl phosphate, luciferin derivative, or dioxetane derivative; or the like. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyases; an isomerase; or a ligase. The enzyme may also be conjugated to another enzyme. The enzyme may be detected by enzymatic cycling. For example, when the detectable label is an alkaline phosphatase, measurements may be made by observing the fluorescence or luminescence generated from a suitable substrate, such as an umbelliferone derivative. The umbelliferone derivative may comprise 4-methyl-umbelliferyl phosphate. The fluorescent or chemiluminescent label may be a fluorescein isothiocyanate; a rhodamine derivative such as rhodamine B isothiocyanate or tetramethyl rhodamine isothiocyanate; a dansyl chloride (5-(dimethylamino)-1-naphtalenesulfonyl chloride); a dansyl fluoride; a fluorescamine (4-phenylspirofuran-2(3H)ly-(3yH)-isobenzofuran 3,3y-dione); a phycobiliprotein such as a phycocyanin or phycoerythrin; an acridinium salt; a luminol compound such as luciferin, luciferase, or aequorin; imidazoles; an oxalic acid ester; a chelate compound of rare earth elements such as europium (Eu), terbium (Tb) or samarium (Sm); or a coumarin derivative such as 7-amino-4-methylcoumarin. The label may also be a hapten, such as adamantine, fluorescein isothiocyanate, or carbazole. The hapten may allow the formation of an aggregate when contacted with a multi-valent antibody or (strep)avidin containing moiety. Further examples of detectable moieties include, but are not limited to, the following: radioisotopes, e.g. $^{3}H$, $^{14}C$, $^{35}S$, $^{123}I$, $^{125}I$, $^{131}I$, $^{99}Tc$, $^{111}In$, $^{90}Y$, $^{188}Re$; radionuclides, e.g. $^{11}C$, $^{3}H$, $^{18}F$, $^{64}Cu$; fluorescent labels, e.g. FITC, rhodamine, lanthanide phosphors, carbocyanine; enzymatic labels; e.g. horseradish peroxidase, β-galactosidase, luciferase, alkaline phosphatase; chemiluminescent, biotinyl groups and predetermined polypeptide epitopes recognized by a secondary binding entity; e.g. leucine zipper pair sequences; binding sites for secondary antibodies, metal binding domains, epitope or protein tags, carbohydrates. In some embodiments, labels are attached by spacer arms of various lengths to reduce potential steric hindrance.

In indirect labelling, an additional molecule or moiety is brought into contact with, or generated at the site of, oligothiophene derivative—neural stem cell or oligothiophene derivative—neural stem cell complexes. For example, a detectable moiety such as an enzyme can be attached to or associated with the detecting oligothiophene derivative as exemplified herein. The signal-generating molecule can then generate a detectable signal at the site of the complex. For example, an enzyme, when supplied with suitable substrate, can produce a visible or detectable product at the site of the complex.

As another example of indirect labelling, an additional molecule (which can be referred to as a binding agent) that can bind to either the target motif of interest or to the oligothiophene derivative of interest and can be contacted with the complex. The additional molecule can have signal-generating molecule or detectable moiety. The additional molecule can also be or include one of a pair of molecules or moieties that can bind to each other, such as the biotin/avidin molecules, and the detecting antibody or detecting molecule should then include the other member of the pair.

This system may further comprise means to provide for signal amplification. Examples of binding agents with means for signal amplification are oligothiophene derivatives according to the invention such as biotinylated oligothiophene derivatives (e.g., conjugated with avidin/streptavidin) or staphylococcal Protein A (binds IgG), Protein G, dextran, aptamers, proteins, peptides, small organic molecules, natural compounds (e.g. steroids), non-peptide polymers, or any other molecules that specifically and efficiently bind to other molecules conjugated with a detectable moiety of not.

The oligothiophene derivative described herein may be lyophilized for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of activity loss and that use levels may have to be adjusted upward to compensate. In one embodiment, the lyophilized (freeze dried) composition loses no more than about 20%, or no more than about 25%, or no more than about 30%, or no more than about 35%, or no more than about 40%, or no more than about 45%, or no more than about 50% of its activity (prior to lyophilisation) when re-hydrated.

Thus, as revealed herein, said compositions of the invention are any oligothiophene derivative disclosed herein, such as the ones selected from the group consisting of a) an oligothiophene derivative according to formula (I)

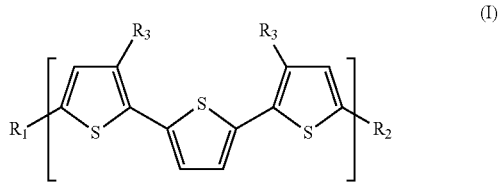

wherein
R₃ may be chosen from

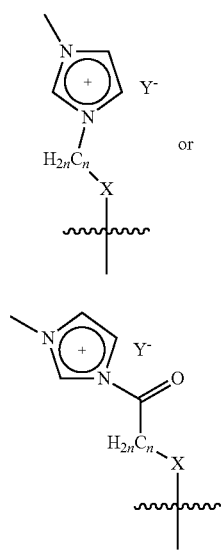

and wherein n may vary from 0 to 3,

Y⁻ is the anionic counter ion and may be but is not limited to bromine, chlorine, iodine or 4-methylbenzenesulfonate, X may be chosen from O (n≥1) or CH₂ (n=0-3), and each $R_1$ and $R_2$ is independently selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of ¹⁸F or ¹⁹F (10), 5-thiophene-2-yl with tritium (11) and 5-methylthiophene-2-yl with ¹¹C (12) according to the formulas

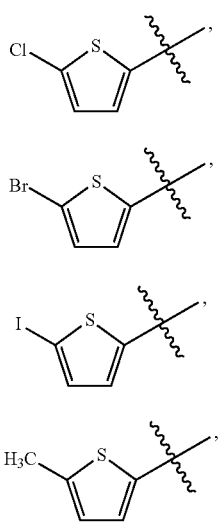

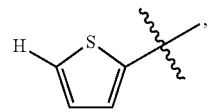

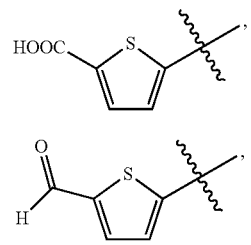

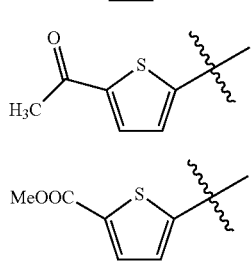

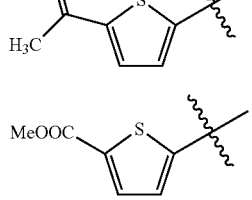

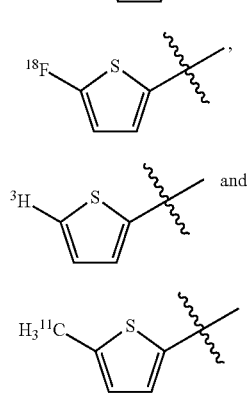

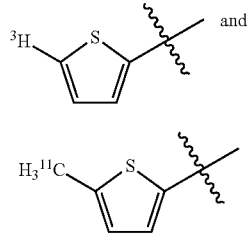

b) oligothiophene derivate according to formula (I),

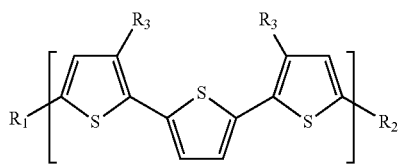

wherein R1 is

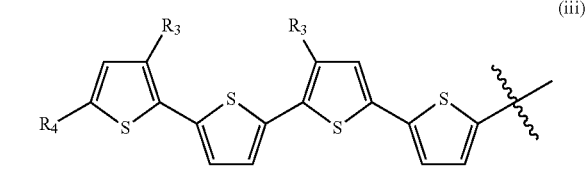

and wherein n may vary from 0 to 3,

Y⁻ is the anionic counter ion and may be but is not limited to bromine, chlorine, iodine or 4-methylbenzenesulfonate, and X may be chosen from O (n≥1) or CH$_2$ (n≥0) and R2 is selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with $^{11}$C (12) according to the formulas

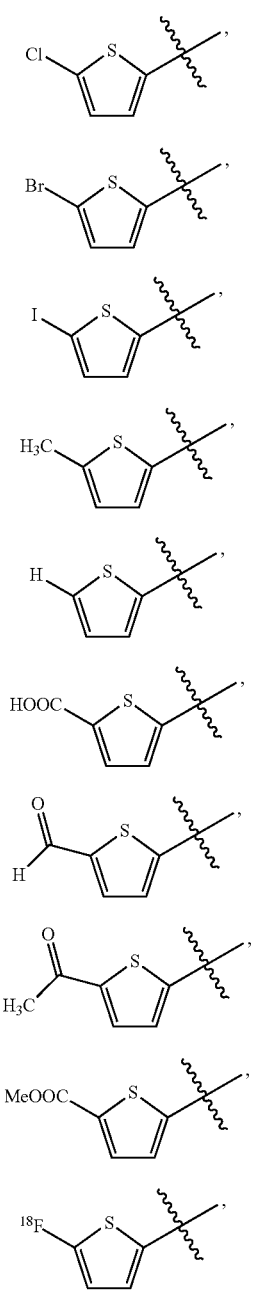

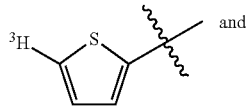

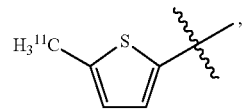

R3 is chosen from

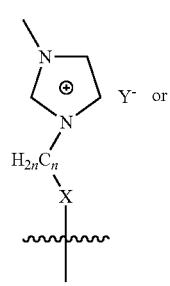

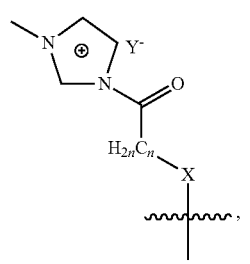

and

R$_4$ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with $^{11}$C (12) according to the formulas:

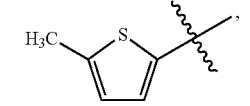

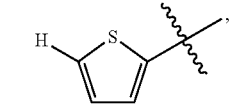

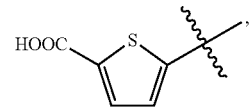

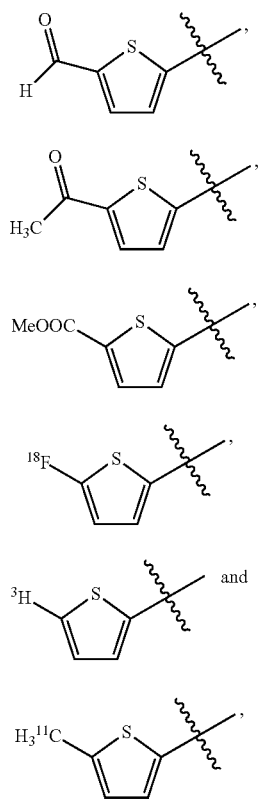

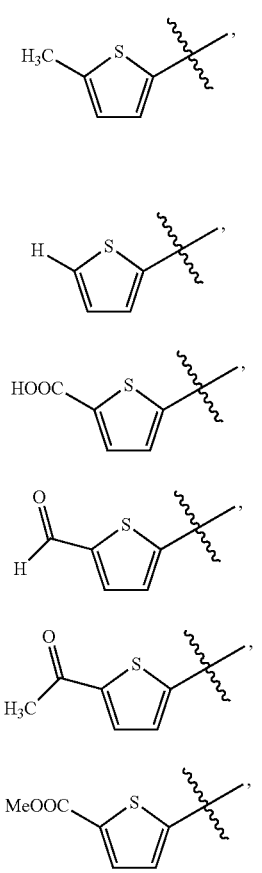

and
c) according to formula (I),

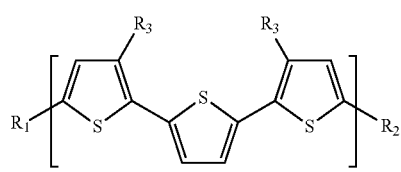

wherein $R_1$ is formula (iii)

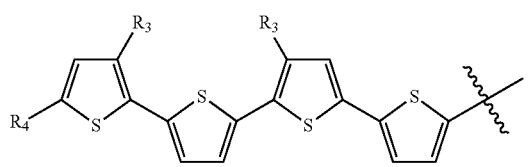

and wherein $R_2$ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas:

R3 is chosen from

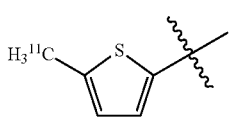

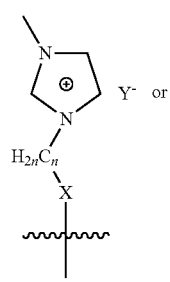

-continued

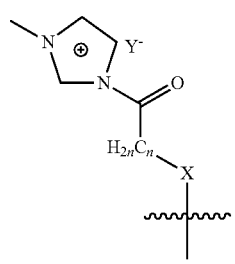
(ii)

and wherein n may vary from 0 to 3,

Y⁻ is the anionic counter ion and may be but is not limited to bromine, chlorine, iodine or 4-methylbenzenesulfonate, X may be chosen from O (n≥1) or CH$_2$ (n=0-3), and R4 is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with $^{11}$C (12) according to the formulas:

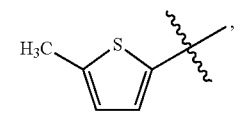
4

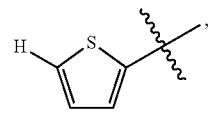
5

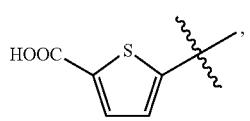
6

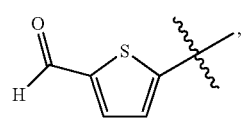
7

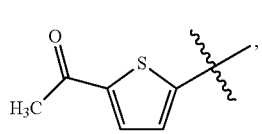
8

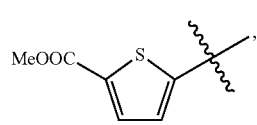
9

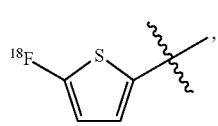
10

-continued

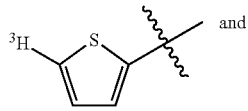
11 and

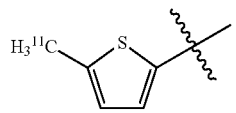
12 and of all the oligothiophene derivative according to the invention pharmaceutically acceptable salts thereof.

Further embodiments are wherein said oligothiophene derivative is an oligothiophene derivative according to formula (I)

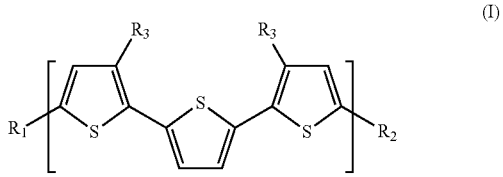
(I)

wherein
R$_3$ may be chosen from

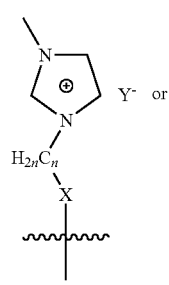
(i)

or

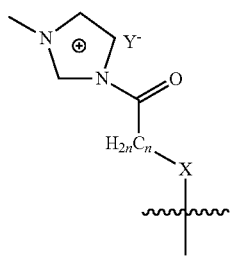
(ii)

and wherein
n may vary from 0 to 3,

Y⁻ is the anionic counter ion and may be but is not limited to bromine, chlorine, iodine or 4-methylbenzenesulfonate, X may be chosen from O (n≥1) or CH$_2$ (n=0-3), and each R$_1$ and R$_2$ is independently selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with $^{11}$C (12) according to the formulas

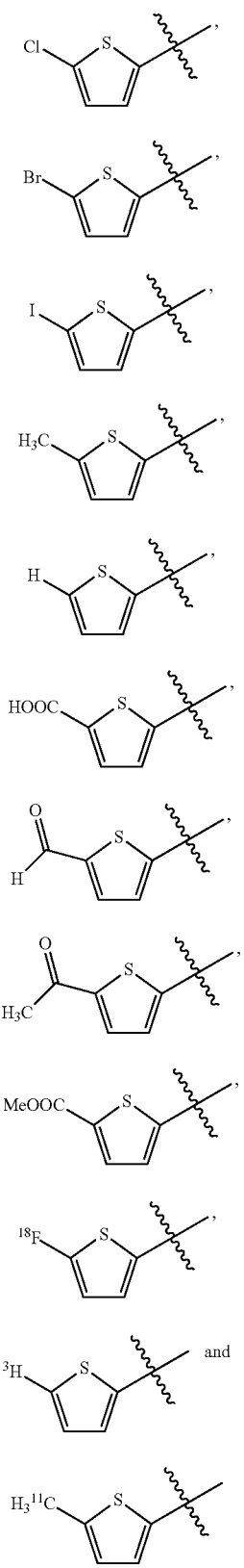

Further embodiments are wherein said oligothiophene derivative is an oligothiophene derivate according to formula (I),

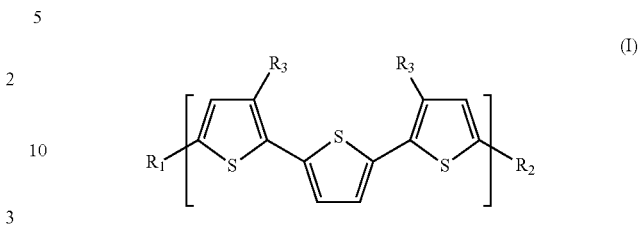

wherein R1 is

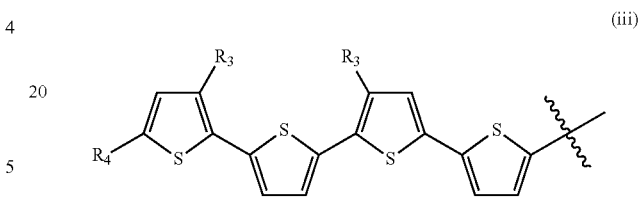

and wherein
n may vary from 0 to 3,
$Y^-$ is the anionic counter ion and may be but is not limited to bromine, chlorine, iodine or 4-methylbenzenesulfonate, and
X may be chosen from O (n≥1) or $CH_2$ (n≥0) and
R2 is chosen from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas

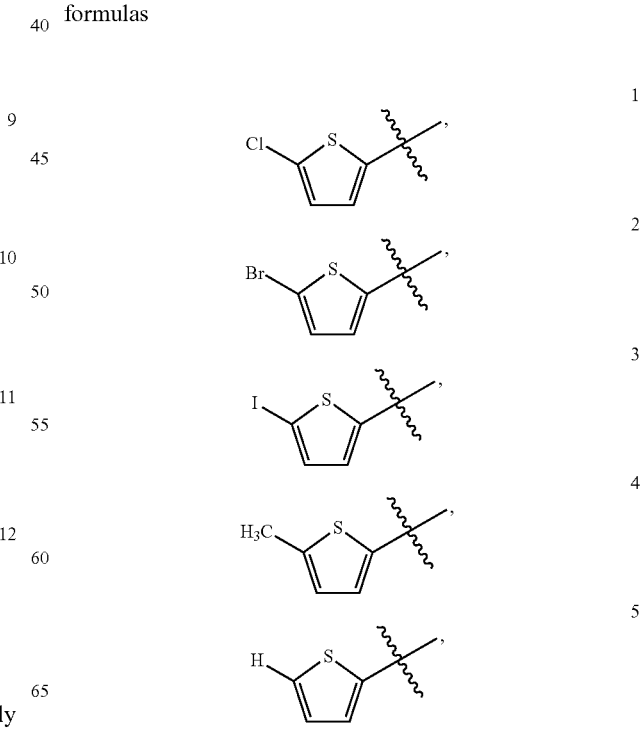

and of all the oligothiophene derivative pharmaceutically acceptable salts thereof.

-continued

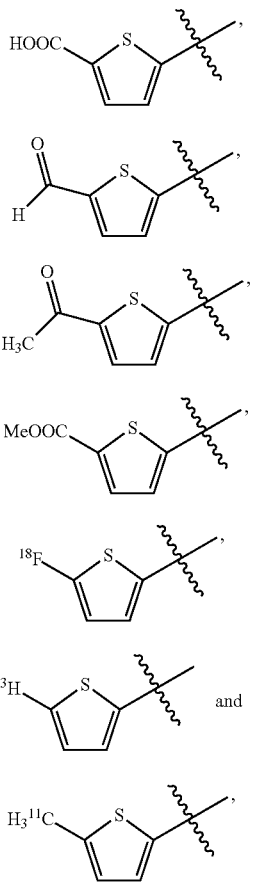

R3 is chosen from

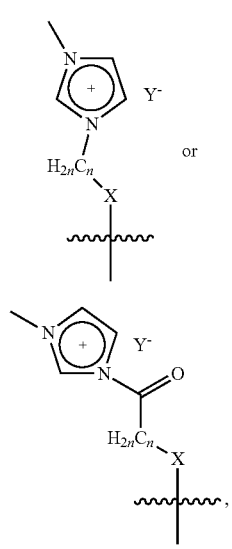

and
R₄ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas:

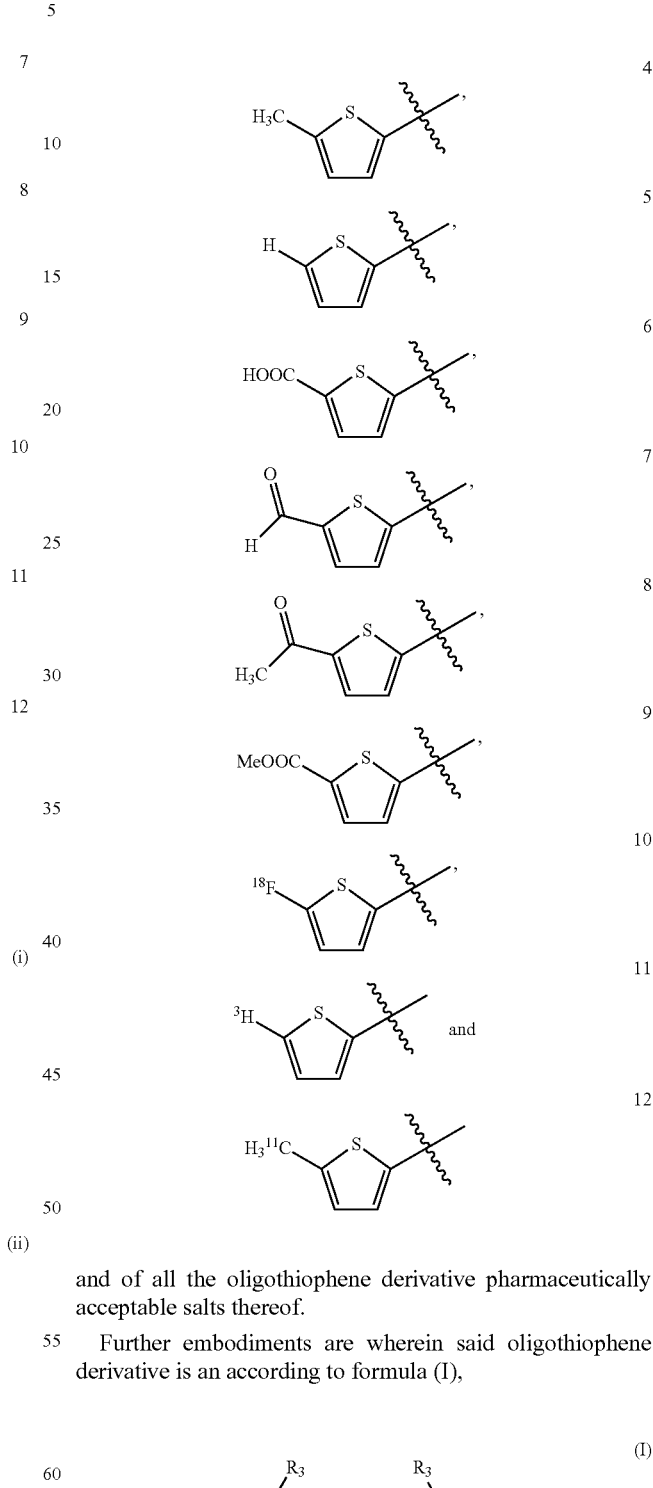

and of all the oligothiophene derivative pharmaceutically acceptable salts thereof.

Further embodiments are wherein said oligothiophene derivative is an according to formula (I),

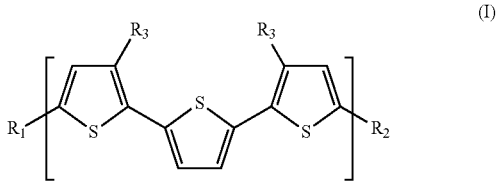

wherein R₁ is formula (iii)

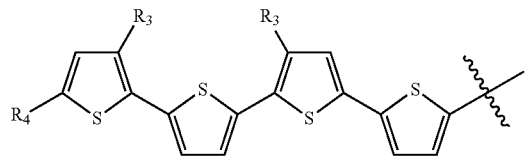
(iii)

and wherein $R_2$ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas:

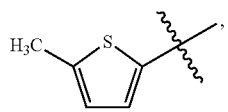
4

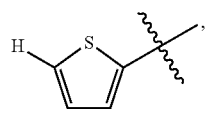
5

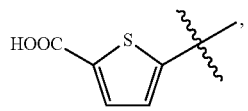
6

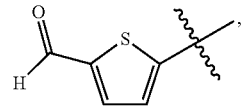
7

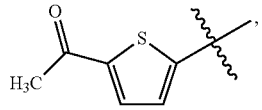
8

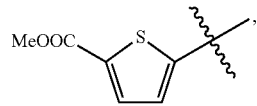
9

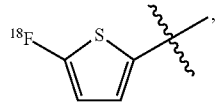
10

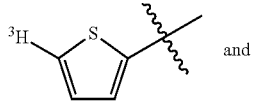
11
and

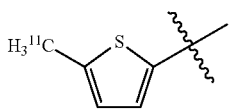
12

R3 is chosen from

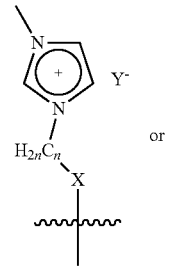
(i)

or

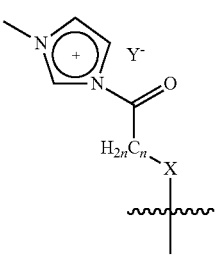
(ii)

and wherein n may vary from 0 to 3, $Y^-$ is the anionic counter ion and may be but is not limited to bromine, chlorine, iodine or 4-methylbenzenesulfonate, X may be chosen from O (n≥1) or $CH_2$ (n=0-3), and $R_4$ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas:

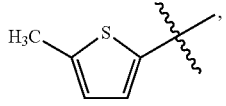
4

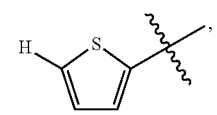
5

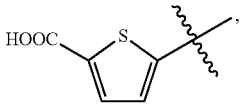
6

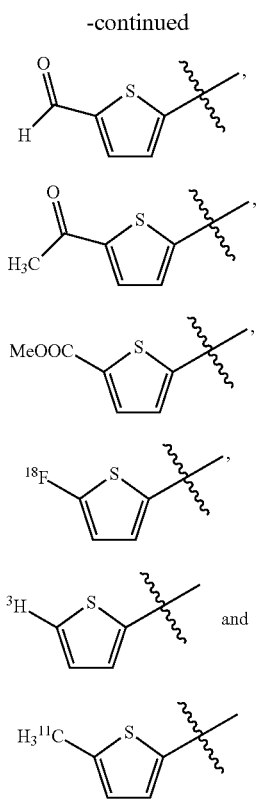

and of all the oligothiophene derivative pharmaceutically acceptable salts thereof.

A Composition

A further aspect of the present invention provides a composition. Said composition may be used for detecting, identifying, separating and isolation of neural stem cells or neural cancer stem cells.

In further embodiments, the neural stem cells are adult neural stem cells, such as adult human neural stem cells.

In further embodiments, the neural stem cells are embryonic neural stem cells, such as e.g. rat embryonic neural stem cells or any other rodent embryonic neural stem cells. In still further embodiments, the embryonic neural stem cells are non-human embryonic neural stem cells. In still further embodiments, the embryonic neural stem cells are human embryonic neural stem cells.

In still further embodiments, the neural cancer stem cells are adult neural cancer stem cells.

The composition comprises any of the oligothiophene derivatives according to the invention.

The composition provided herein further comprises a buffer. Examples of buffers are Tris-buffers such as Tris-HCl, and PBS-buffers. Suitable buffers are available and known in the art and examples are given in e.g. Current Protocols in Immunology, and Current Protocols in Molecular Biology, both John Wiley and Sons, Inc., N.Y.) incorporated herein by reference.

Further additives to the buffers may be e.g. Tween® 20, BSA, sodium azide, glycerol, and water, and a pH of about 5.5 to 7.5, such as 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5.

The oligothiophene derivative and its corresponding composition may when in a liquid form be provided in a "ready-to-use" form or in a concentrated form which may be diluted before use in any appropriate buffer system upon use, for example at least 1×10, 1×20, 1×30, 1×40, 1×50, 1×60, 1×70, 1×80, 1×90, 1×100, 1×150, 1×200, 1×250, 1×300, 1×350, 1×400, 1×450, 1×500, 1×550, 1×600, 1×650, 1×700, 1×750, 1×800, 1×900, 1×1000, 1×1200, 1×1500, 1×2000, 1×3000, 1×4000, 1×5000, 1×6000, 1×7000, 1×8000, 1×9000, 1×10000 and all ranges and values there between such as in e.g. the buffer systems provided herein or that may be apparent to a person skilled in the art.

The oligothiophene derivative and its corresponding composition according to the invention may also be used alone or in combination with other means for detecting neural stem cells or neural cancer stem cells. Said cells may be of mammal origin, such as rodent, e.g. mice, rats, squirrels, porcupines, beavers, guinea pigs, and voles, or non-rodents such as goat, pig, feline, cow, dog, or human cells, such as e.g. adult human neural stem cells or adult human neural cancer stem cells. Other means to detect neural stem cells or neural cancer stem cells in combination with oligothiophene derivatives of the invention include e.g. antibodies binding specifically to antigens on neural stem cells. General protocols for such antibody-based immuno-methods are known in the art (Antibodies: A Laboratory Manual, Harlow and Lane, Cold Spring Harbor Laboratory press, Cold Spring Harbor, N.Y. 1988, Current Protocols in Immunology, Unit 21.4, 2003, and Current Protocols in Molecular Biology, Unit 14.6, 2001, both John Wiley and Sons, Inc., N.Y.).

Methods

A further aspect of the present invention provides a method for detecting neural stem cells or neural cancer stem cells in a biological sample in vitro or in vivo, the method comprising the steps of a. contacting said sample with an oligothiophene derivate according to the invention or a composition comprising at least one oligothiophene derivate according to the invention or the composition according to the invention, for sufficient time to form at least one neural stem cell-oligothiophene derivate complex, b. detecting said neural stem cell-oligothiophene derivate complexes.

Further steps of the method may encompass comparing the amount of neural stem cell-oligothiophene derivate complexes detected to a positive and/or negative control, thereby detecting the neural stem cells. This is normally done to set background levels of a staining in a particular example or experimental set up and to be able to score a positive staining from a negative, to assess that the method has performed accordingly as expected and that a positive staining is a true detection of said neural stem cell.

Further, said neural stem cell may be a neural cancer stem cell.

Further, changes in numbers or amounts of neural stem cells or neural cancer stem cells may be detected. Changes in numbers or amounts may be an increase in neural stem cells or neural cancer stem cells or a decrease of neural stem cells or neural cancer stem cells.

Further, the positive control may comprise neural stem cells, neural cancer stem cells or parts thereof. Parts thereof may be cell fragments, lysed cells, etc. wherein the parts thereof still comprises the motif whereto the oligothiophene derivative or the composition according to the invention still binds.

Further, the negative control may not comprise neural stem cells, neural cancer stem cells, or a part thereof whereto the oligothiophene derivative or the composition according to the invention still binds.

Said methods may further comprise a step of optionally scoring the amount of neural stem cells-oligothiophene derivate complexes, or neural cancer stem cell-oligothiophene derivative complexes. A scoring may be done of the detected neural stem cell-oligothiophene derivative complexes or neural cancer stem cell-oligothiophene derivative complexes according to a standard scoring system known in the art or described herein.

Detecting the neural stem cells-oligothiophene derivate complexes can be achieved using methods well known in the art of cell detection and imaging such as clinical imaging further described herein and in the art, such as conventional fluorescence microscopes, confocal microscopes, 2-photon microscopes, STED etc. The specific method required will depend on the specific luminescence of the oligothiophene derivative and/or the type of detectable label/conjugate attached to the oligothiophene derivative of the invention.

After removal of a brain tumour by surgery, the oligothiophene derivate according to the invention may be used as to detect residual neural cancer stem cells. This may be done by contacting the space where the brain tumour has been removed from, by applying the oligothiophene derivative according to the invention to the cavity appearing after the tumour removal. The oligothiophene derivative may be added by brushing or equally applying the oligothiophene derivative according to the invention to the cavity in the brain where the tumour was located. Thus, the applied oligothiophene derivative will detect residual neural cancer stem cells—if any—in the cavity left after removal of a tumour in a brain.

A number of approaches have been developed for non-invasive measurements and detection of tissues or of cells in vivo. These approaches have generally used techniques of nuclear medicine to generate images of a variety of tissues or individual cells. Such non-invasive imaging methods include positron emission tomography (PET) and single photon emission computed tomography (SPECT). A wide variety of radiopharmaceuticals have been successfully employed in PET and SPECT imaging studies.

Thus, it is of great value in clinical practice to be able to rapidly and noninvasively assess the effectiveness of e.g. a surgery to remove a brain tumour such as glioma or to detect the effectiveness and response of a brain tumour in vivo to one or a combination of chemotherapeutic agents in each patient undergoing treatment. It would also be of great value to be able to predict the outcome of treatment based on quantitative measurements of tumour response after initiation of chemotherapy. Prompt feedback provided by early and frequent monitoring after the initiation of therapy would enable the oncologist to ascertain the effectiveness of the selected regimen and to modify it if the disease is not responding appropriately. Using non-invasive assessment of tissue response, the time necessary to determine the efficacy of a particular regimen may also be sharply reduced, lowering the risk that the cancer will have grown or metastasized in the interim.

Thus, further embodiments are wherein PET may be used to detect the residual neural cancer stem cells in said cavity after removal of the tumour.

Thus, further embodiments are wherein the detection of neural cancer stem cells is done by PET, using a dedicated PET scanner of a subject such as a rodent, e.g. rat or mouse, or a human being. PET scanning is non-invasive, but it does involve exposure to ionizing radiation. The total dose of radiation is not insignificant, usually around about 11 mSv.

Alternative methods of scanning useful in further embodiments as an alternative to PET include x-ray computed tomography (CT), magnetic resonance imaging (MRI) and functional magnetic resonance imaging (fMRI), ultrasound and single photon emission computed tomography (SPECT).

The methods provided herein may be performed manually, or, preferably, on an automated device.

Thus, in one embodiment the methods are performed manually.

In a further embodiment, the methods are performed in an automated device.

In general, the dyes are stored in a small plastic tube and applied to a biological sample being e.g. a cell culture or cell sample, cells in a solution, and/or to a tissue, directly with a pipette. After 5-60 minutes incubation (usually around 10 minutes), the neural stem cells or neural cancer stem cells are readily detectable in various conventional microscopes and in cell sorting applications, such as fluorescence-assisted cell sorting such as e.g. fluorescence activated cell sorting (FACS). No modulation is required and all procedures can be performed at room temperature in a normal laboratory.

The methods provided herein may be used in tissue micro arrays. Tissue micro arrays are also known and described in the art. Typically, tissue micro arrays may typically contain 50 to 500 tissues on a single slide.

Examples of automated staining devices useful to screen tissue samples and tissue slices, such as explants, according to the present invention are to include, but not limited to, Dako Autostainer (DakoCytomation), BioGenex 16000™ (Biogenex), Nemesis™ (BIOCARE), and NexES, Benchmark, Capilary gp stainer (Ventana systems). The sample is then ready for visualisation, detection, an optional scoring and further analysis.

The methods according to the invention may be a method which is performed on an automated staining device.

In still further embodiments, the methods are performed manually.

Tissue sections to be stained are frequently about 5-100 µm, such as e.g. 10-40 µm, i.e. tissue sections used normally for histology analysis such as immunohistochemistry.

However, tissue sections may be thicker, about >100 µm or more, like tissue slices or explants.

The detection may be made manually, such as by a pathologist or a medical doctor or anyone equally trained staff to manually view and detect neural stem cells or neural cancer stem cells by scoring.

Thus, further embodiments are wherein the detection is made manually, e.g. by for example scoring in microscope.

The detection may further be done by image analysis. Suitable image analysis devices useful according to the present invention are known in the art and also exemplified herein.

Thus, further the detection may be made by image analysis in vivo, in situ or in vitro.

Still a further aspect of the invention provides a method for separating neural stem cells from other biological material in a biological sample, the method comprising the steps of a. contacting said sample with an oligothiophene derivate according to the invention or the composition according to the invention, for sufficient time to form at least one neural stem cell-oligothiophene derivate complex, b. detecting said neural stem cell-oligothiophene derivate complexes, c. separating said detected neural stem cell-oligothiophene derivate complexes, thereby separating neural stem cells.

Further, said neural stem cell may be a neural cancer stem cell.

The neural stem cell or neural cancer stem cell may further be an adult neural stem cell or adult neural cancer stem cell.

The method may further comprise the step of isolating said neural stem cells or neural cancer stem cell, such as e.g. adult neural stem cell or adult neural cancer stem cell.

The separation of neural stem cells may be a selection step which may be followed by an isolation step for separating the identified neural stem cells or neural cancer stem cell. Various techniques known to the skilled artisan may be employed to separate the cells by initially removing cells dedicated to other lineages than neural stem cells. Often, such methods are based on density centrifugation as well as different immuno-methods using lineage specific antibodies.

Thus, for the separation, the oligothiophene derivative according to the invention may be attached to a solid support to allow for a highly specific separation of said neural stem cells or neural cancer stem cells, such as e.g. adult neural stem cells or adult neural cancer stem cells. The particular procedure for separation employed, e.g. centrifugation, mechanical separation, such as columns, membranes or magnetic separation, should maximize the viability of the fraction to be collected. Various techniques of different efficacy may be employed and are well known to a person skilled in the art. The particular technique employed will depend upon efficiency of separation, cytotoxicity of the methodology, ease and speed of performance, and necessity for sophisticated equipment and/or technical skill of the staff using the technique.

Procedures for separation of neural stem cells or neural cancer stem cells from a cell suspension aided by the oligothiophene derivative according to the invention may include magnetic separation, using e.g. oligothiophene derivative-coated magnetic beads, affinity chromatography based on the oligothiophene derivative according to the invention, and "panning" with oligothiophene derivative thereof attached to a solid matrix, e.g., a plate, or other convenient techniques. Magnetic cell sorting are well known to a person skilled in the art and is described in, for example, Haukanes and Kvam (1993) Biotechnology 11(1):60-63, and Quirici et al (2002) Exp. Hematol 30:783-791.

Thus, the oligothiophene derivative according to the invention used in a positive selection is linked to a solid phase. Examples of solid phases to be used are Protein A or Protein G, activated beads such as agarose beads, cross-linked agarose beads, polyacrylamide beads, copolymers of polyacrylamide and agarose beads or polyacrylic beads.

The solid phase may be a bead. Beads are activated with, for example Carbonyldiimadazole, Cyanogen bromide and by other similar methods well known to a skilled man in the art and further exemplified by Harlow and Lane, 1988, included herein by reference.

Further, the solid phase may a magnetic bead. Cells can then be sorted using magnetic cell sorting, such as the MACS® system.

Techniques providing accurate separation include fluorescence activated cell sorters by the use of the oligothiophene derivative according to the invention, which can have varying degrees of sophistication, e.g., a plurality of colour channels, light scattering detecting channels, impedance channels, etc. known to the skilled man in the art.

The isolation may further be done by mechanical means, such as e.g. panning, beads or affinity columns.

The isolation may further be done by flow cytometric means such as FACS.

A stepwise isolation and separation may take place. For example, a first enrichment step of neural stem cells or neural cancer stem cells in a biological sample, such as a cell population, is made. This first selection may be a negative selection of the neural stem cells, i.e. other lineage-committed cells are depleted, or removed, from the initial population of cells.

Said first enrichment may be a positive selection of neural stem cells or neural cancer stem cells that may be repeated until the desired purity of the neural stem cells is achieved.

Neural stem cells or neural cancer stem cells may be isolated from brain tissue samples such as adult mammal brain, e.g. rodent brain (mice or rat) or human brain. Alternatively, neural stem cells may be derived from embryonic stem (ES) cells or induced pluripotent (iPS) cells from mammals, e.g. rodents or humans.

The method may optionally further comprise recovering cells binding to the oligothiophene derivative thereby producing a population of neural stem cells or neural cancer stem cells, substantially free from contaminating cells of other lineages, such as 90%, 95%, 99% or even 100% free from contaminating cells of other lineages.

Further aspects of the invention provide methods for synthesising an oligothiophene derivative according to the invention.

Further aspects of the invention are uses of the oligothiophene derivatives according to the invention or the composition according to the invention, to detect, identify, select and isolate neural stem cells in vitro, in situ or in vivo.

Data analysis to analyse the presence or absence of neural stem cells using the oligothiophene derivative or the composition of the invention may include the steps of determining signal strength (e.g., intensity of peaks) of the luminescence from the oligothiophene derivative, or any other means conjugated directly or indirectly to the oligothiophene derivative, and removing "outliers" (data deviating from a predetermined statistical distribution). An example is the normalization of peaks, a process whereby the intensity of each peak relative to some reference is calculated. For example, a reference can be background noise generated by an instrument and/or a chemical (e.g., energy absorbing molecule), which is set as zero in the scale. Then the signal strength detected for each neural stem cell-oligothiophene derivative complex or neural cancer stem cell-oligothiophene derivative can be displayed in the form of relative intensities in the scale desired (e.g., 100). In an embodiment, an observed signal for a given peak can be expressed as a ratio of the intensity of that peak over the sum of the entire observed signal for both peaks and background noise in a specified mass to charge ratio range. In an embodiment, a standard may be admitted with a sample so that a peak from the standard can be used as a reference to calculate relative intensities of the signals observed for each protein detected.

The resulting data can be transformed into various formats for displaying, typically through the use of computer algorithms. Using any of the above display formats, it can be readily determined from a signal display whether said neural stem cells or neural cancer stem cells are detected in a sample or not.

Kits

Further aspects provides a kit comprising
a. an oligothiophene derivatives according to the invention or a composition according to the invention, and
b. optionally, instructions for using the oligothiophene derivate or the composition.

Further aspects of the invention provides a kit for detecting neural stem cells or neural cancer stem cells in vitro, in situ or in vivo, the kit comprising
a. an oligothiophene derivate according to the invention or the composition according to the invention, and
b. optionally, instructions for using the oligothiophene derivate or the composition.

Further aspects of the invention provides a kit for separating neural stem cells or neural cancer stem cells, the kit comprising a. an oligothiophene derivate according to the invention or the composition according to the invention, and
   b. optionally, instructions for using the oligothiophene derivate.

Thus, as revealed herein, said compositions of the invention are any oligothiophene derivative disclosed herein, such as the ones selected from the group consisting of a) an oligothiophene derivative according to formula (I)

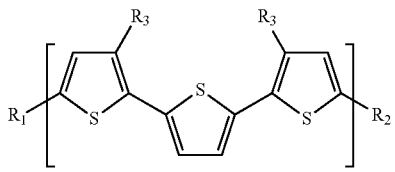

(I)

wherein
$R_3$ may be chosen from

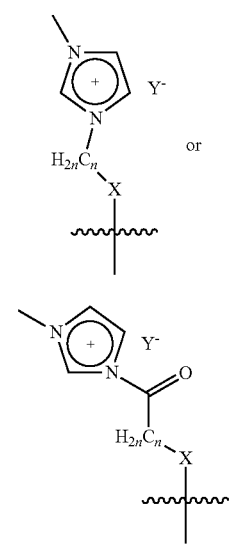

(i)

or (ii)

and wherein
n may vary from 0 to 3,
$Y^-$ is the anionic counter ion and may be but is not limited to bromine, chlorine, iodine or 4-methylbenzenesulfonate,
X may be chosen from O (n≥1) or $CH_2$ (n=0-3), and
each $R_1$ and $R_2$ is independently selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas

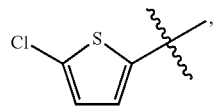

1

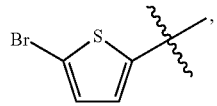

2

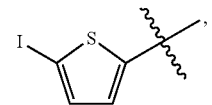

3

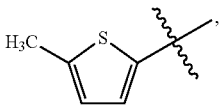

4

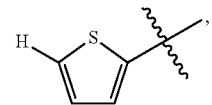

5

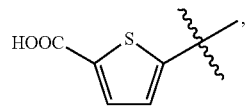

6

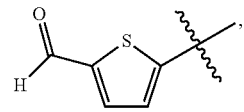

7

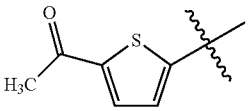

8

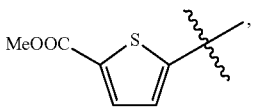

9

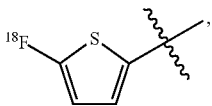

10

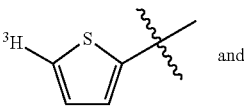

and

11

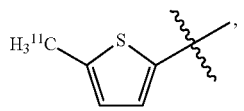

12 b) oligothiophene derivate according to formula (I),

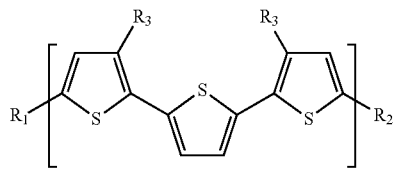

(I)

wherein R1 is

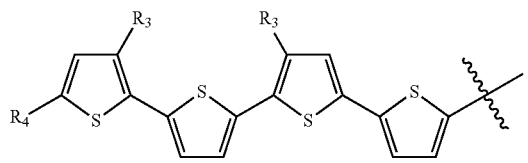

(iii)

and wherein n may vary from 0 to 3,

Y⁻ is the anionic counter ion and may be but is not limited to bromine, chlorine, iodine or 4-methylbenzenesulfonate, and X may be chosen from O (n≥1) or $CH_2$ (n≥0) and $R_2$ is chosen from 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas

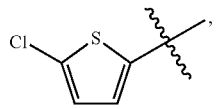
1

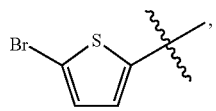
2

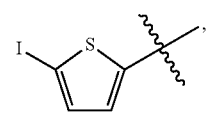
3

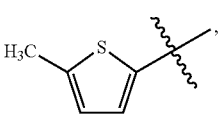
4

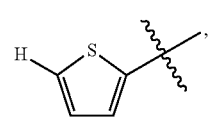
5

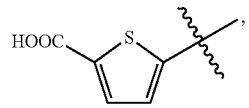
6

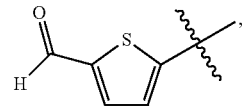
7

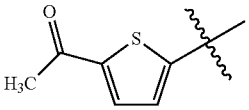
8

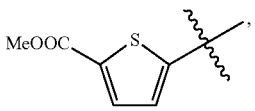
9

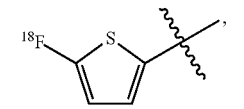
10

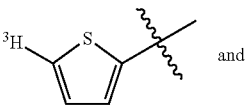 and
11

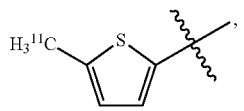
12

R3 is chosen from

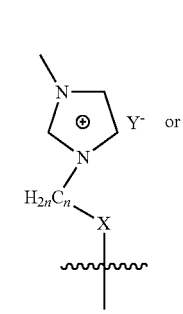

(i)

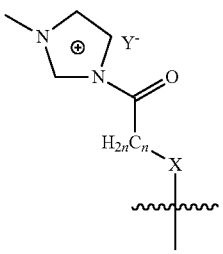

(ii)

and wherein n may vary from 0 to 3,

Y⁻ is the anionic counter ion and may be but is not limited to bromine, chlorine, iodine or 4-methylbenzenesulfonate, X may be chosen from O (n≥1) or CH$_2$ (n=0-3), and R$_4$ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with $^{11}$C (12) according to the formulas:

4
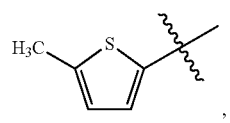

5
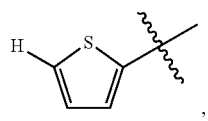

6
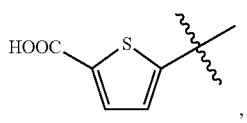

7
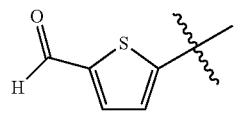

8
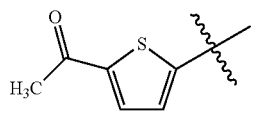

9
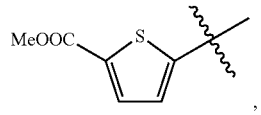

10
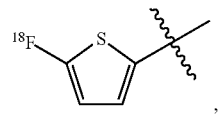

11
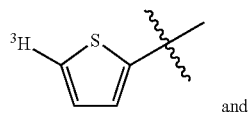
and

12
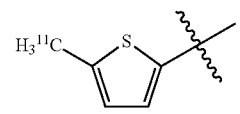

c) according to formula (I),

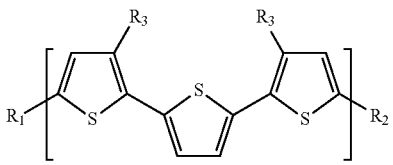
(I)

wherein R$_1$ is formula (iii)

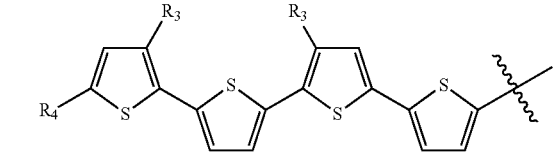
(iii)

and wherein R$_2$ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with $^{11}$C (12) according to the formulas:

4
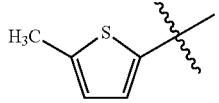

5
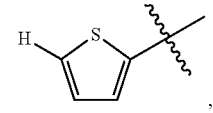

6
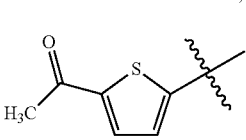

7
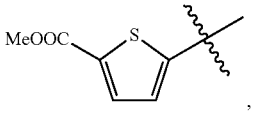

8

9

-continued

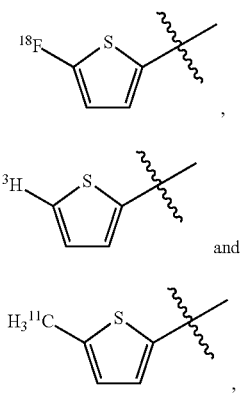

R3 is chosen from

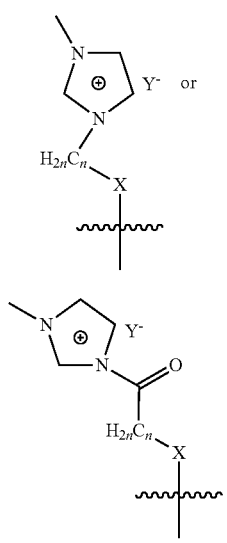

and wherein n may vary from 0 to 3,

Y⁻ is the anionic counter ion and may be but is not limited to bromine, chlorine, iodine or 4-methylbenzenesulfonate, X may be chosen from O ($n \geq 1$) or $CH_2$ (n=0-3), and R4 is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with $^{11}C$ (12) according to the formulas:

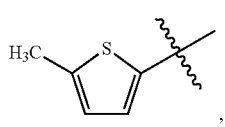

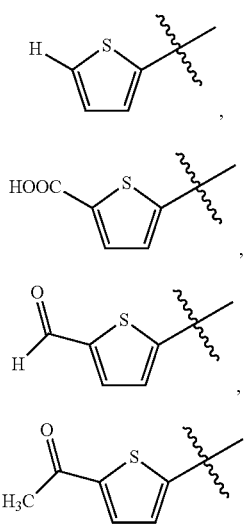

and of all the oligothiophene derivative according to the invention pharmaceutically acceptable salts thereof.

The kit according to the invention may further comprise means to isolate said neural stem cells or neural cancer stem cells.

Further, said kit may include positive or negative control samples, such as a cell line or tissue known to express or not express neural stem cells or neural cancer stem cells. Examples of control samples include but are not limited to normal cells or tissues from brain, such as a human brain, cell lines of neural stem cell origin, or neural cancer stem cell origin. In further embodiments, the brain cells or cell lines are of adult origin.

In some embodiments, a kit includes instructional materials disclosing, for example, means of use of the oligothiophene derivative according to the invention or a composition according to the invention, detection means, or means of use for a particular reagent. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method.

Such kits and appropriate contents are well known to those of skill in the art.

The kit may further comprise, in an amount sufficient for at least one assay, the oligothiophene derivative according to the invention or the composition according to the invention as a separately packaged reagent.

Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

Certain kit embodiments can include a carrier means, such as a box, a bag, a satchel, plastic carton (such as moulded plastic or other clear packaging), wrapper (such as, a sealed or sealable plastic, paper, or metallic wrapper), or other container.

In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

Non-limiting examples which embody certain aspects of the invention will now be described.

EXAMPLES

Example 1

Staining of Undifferentiated Immature Neural Stem Cells and Differentiated and More Mature Neural Cells Cell Culture and Plate Preparation NSCs were dissociated and isolated from the cerebral cortices of E15.5 embryos of timed pregnant Sprague-Dawley rats. Animals were treated in accordance with institutional and national guidelines (Ethical permit no. N310/05).

Tissue culture plates were first coated with 15 µg/ml poly-1-ornithine (Sigma-Aldrich) for 1 h, and then rinsed with PBS three times.

Next, the plates were coated with 1 µg/ml fibronectin (Sigma-Aldrich) for 1 h and then rinsed once in PBS.
Staining of Rat Neural Stem Cells (NSCs)

Neural stem cells were plated in a 6-well plate (40 000 cells/well) in Serum-free DMEM:F12 (Invitrogen) with supplements and 10 ng/ml FGF2 (R&D systems) for 24 h prior to further stimulation.

Cells were then stimulated with 10 ng/ml FGF2, 10 ng/ml CNTF (R&D systems), 10% FBS (Invitrogen), 1 mM VPA (Sigma) or without added factors (N2 medium) for three days.

Addition of soluble factors was carried out every 24 h, and media was changed every 48 h. P-HTMI was administered, at a dilution of 1:500, directly to each well and the detection was done after 10 minutes in a fluorescent microscope.

p-HTMI generated chemiluminescence at a wavelength common to green fluorescent proteins.
Results A strong green signal was obtained in undifferentiated immature stem cells, accumulated in the cytoplasm of the cells, whereas differentiated and more mature cells displayed a significantly lower or no signal.
NSC Treated with BMP4 and Wnt3

Neural stem cells were also treated with 10 ng/ml BMP4 and 10 ng/ml Wnt3a (R&D Systems) for 14 days and then stained with P-HTMI. The mature neurons displayed very week staining.
Results P-HTMI generated chemiluminescence at a wavelength common to green fluorescent proteins.

A strong green signal was obtained in undifferentiated immature stem cells, accumulated in the cytoplasm of the cells, whereas differentiated and more mature cells displayed a significantly lower or no detectable signal.

Neural stem cells were also treated with the extracellular growth factors BMP4 and Wnt3a for 14 days to induce differentiation into mature and functional neurons, and then stained with p-HTMI as described above. The mature neurons displayed very week staining.
NSCs (FGF): 5+
Astrocytes (CNTF): 2
Neurons (VPA): 2+
Neurons (BMP4/Wnt3a): 2
Smooth muscle cells (FBS): 1

Example 2

Staining of NSCs Derived from Mouse Embryonic Stem (ES) Cells

Embryonic stem (ES) cell lines were grown according to standard protocols. ES cell-derived NSC were generated by re-plating day 7 adherent neural differentiation cultures (typically 2-3×106 cells into a T75 flask) on uncoated plastic in NS-A medium supplemented with modified N2 and 10 ng/ml of both EGF and FGF-2 (NSC expansion medium). Over 3-5 d, cells formed aggregates that, after harvesting and sedimentation to remove debris, subsequently attached to fresh plastic and outgrew NSC. After addition of 0.5 µg/ml of puromycin to differentiating adherent cultures at d 7, 46C-NS cells were generated. Cells were re-plated 3 d later into an uncoated T75 flask in N2B27 media with 10 ng/ml of both EGF and FGF-2 in the absence of puromycin. To derive clonal lines single cells were plated into 96-well microwell plates by limiting dilution. and the presence of one cell per well was scored 1 h after plating.
Results A strong green signal was obtained in undifferentiated immature neural stem cells, accumulated in the cytoplasm of the cells, whereas the undifferentiated ES cells displayed a significantly lower or no signal.

Example 3

Staining of Rat C6 Glioma

C6 glioma is a rat cell line used to as a model system for glioma cells. The cells were grown in DMEM medium (Invitrogen) supplemented with 10% FBS.

For the purpose of maintenance, the C6 glioma cells were grown in 75 cm² flask.

Prior to experiments the cells were split and plated (40 000 cells/well) in a 6-well plate. When stained with P-HTMI (1:500) 1-2% of the cells were clearly stained, whereas 98-99% remained unstained. 1-2% of cells is the estimated proportion of the so called cancer stem cells in a glioma culture.

Example 4

Staining of Rat C6 Glioma Cultured as Neural Stem Cells

C6 glioma cells were cultured with the same protocol as for NSCs, on plates pre-coated with poly-1-ornithine and fibronectin and then grown in N2 medium with supplements.

The cells were plated in a 6-well plate (40 000 cells/well) in Serum-free DMEM:F12 (Invitrogen) with supplements and 10 ng/ml FGF2 (R&D systems) for 24 h prior to further stimulation. Cells were then stimulated with 10 ng/ml FGF2, 10 ng/ml CNTF (R&D systems), 10% FBS (Invitrogen), 1 mM VPA (Sigma) or without added factors (N2 medium) for three days.

Addition of soluble factors was carried out every 24 h, and media was changed every 48 h. P-HTMI was administered, at a dilution of 1:500, directly to each well and the detection was done after 10 minutes in a fluorescent microscope.
Results P-HTMI generated chemiluminescence at a wavelength common to green fluorescent proteins. A strong green signal was obtained in undifferentiated immature stem cells, accumulated in the cytoplasm of the cells, whereas differentiated and more mature cells displayed a significantly lower or no signal. All cells grown in FGF2 displayed strong staining compared the cells in differentiation medium.

Example 5

Staining of Human Glioma Cells

Human glioma cells from patients (humans) are used to study glioma in vitro. The cells were grown in DMEM medium (Invitrogen) supplemented with 10% FBS. For the purpose of maintenance, the C6 glioma cells were grown in 75 cm² flask. Prior to experiments the cells were split and plated (40 000 cells/well) in a 6-well plate.
Results When stained with P-HTMI (1:500) 1-2% of the cells were clearly stained, whereas 98-99% remained unstained. 1-2% of cells is the estimated proportion of the so called cancer stem cells in a glioma culture.

Example 6

Staining of Human Glioma Cells Cultured as NSCs

Human glioma cells from patients were cultured with the same protocol as for NSCs, on plates pre-coated with poly-L-ornithine and fibronectin and then grown in N2 medium with supplements.

The cells were plated in a 6-well plate (40 000 cells/well) in Serum-free DMEM:F12 (Invitrogen) with supplements and 10 ng/ml FGF2 (R&D systems) for 24 h prior to further stimulation.

Cells were then stimulated with 10 ng/ml FGF2, 10 ng/ml CNTF (R&D systems), 10% FBS (Invitrogen), 1 mM VPA (Sigma) or without added factors (N2 medium) for three days.

Addition of soluble factors was carried out every 24 h, and media was changed every 48 h. P-HTMI was administered, at a dilution of 1:500, directly to each well and the detection was done after 10 minutes in a fluorescent microscope.

P-HTMI generated chemiluminescence at a wavelength common to green fluorescent proteins.
Results A strong green signal was obtained in undifferentiated immature stem cells, accumulated in the cytoplasm of the cells, whereas differentiated and more mature cells displayed a significantly lower or no signal.

All cells grown in FGF2 displayed strong staining compared the cells in differentiation medium.

Example 7

2-Photonmicroscopy of Neural Stem Cells Stained with p-HTMI

The emission and transmission wavelengths of P-HTMI were characterized in a 2-photonmicroscope.

NSCs were grown in 35 mm plates (40 000 cells/plate) and were treated with 10 ng/ml FGF2 for 48 hours. Prior to staining the cells, the medium was changed to DMEM:F12 medium without phenol red (Invitrogen) in order to eliminate background signals.

CellTracker (Invitrogen) was administered together with P-HTMI (1:500) in order to be able to find living cells, resulting in a double staining in red (CellTracker) and green (P-HTMI). This demonstrates that P-HTMI staining can be combined with the simultaneous detection of other types of biomarkers.

Example 8

FACS-Sorting of Neural Stem Cells Stained with p-HTMI

Rat embryonic (15.5) NSCs were grown in 35 mm plates (40 000 cells/plate) and were treated with 10 ng/ml FGF2 for 48 hours.

Prior to staining the cells, the medium was changed to DMEM:F12 medium without phenol red (Invitrogen) in order to eliminate background signals. Plates were incubated with P-HTMI for 10 minutes and then incubated with HANKs for five minutes. The cells were then scraped and run through a FACS machine. Analysis was carried out on a FACSCalibur flow cytometer equipped with CellQuest software (Becton Dickinson).
Results Results are shown in FIG. 2.

Figure 2:
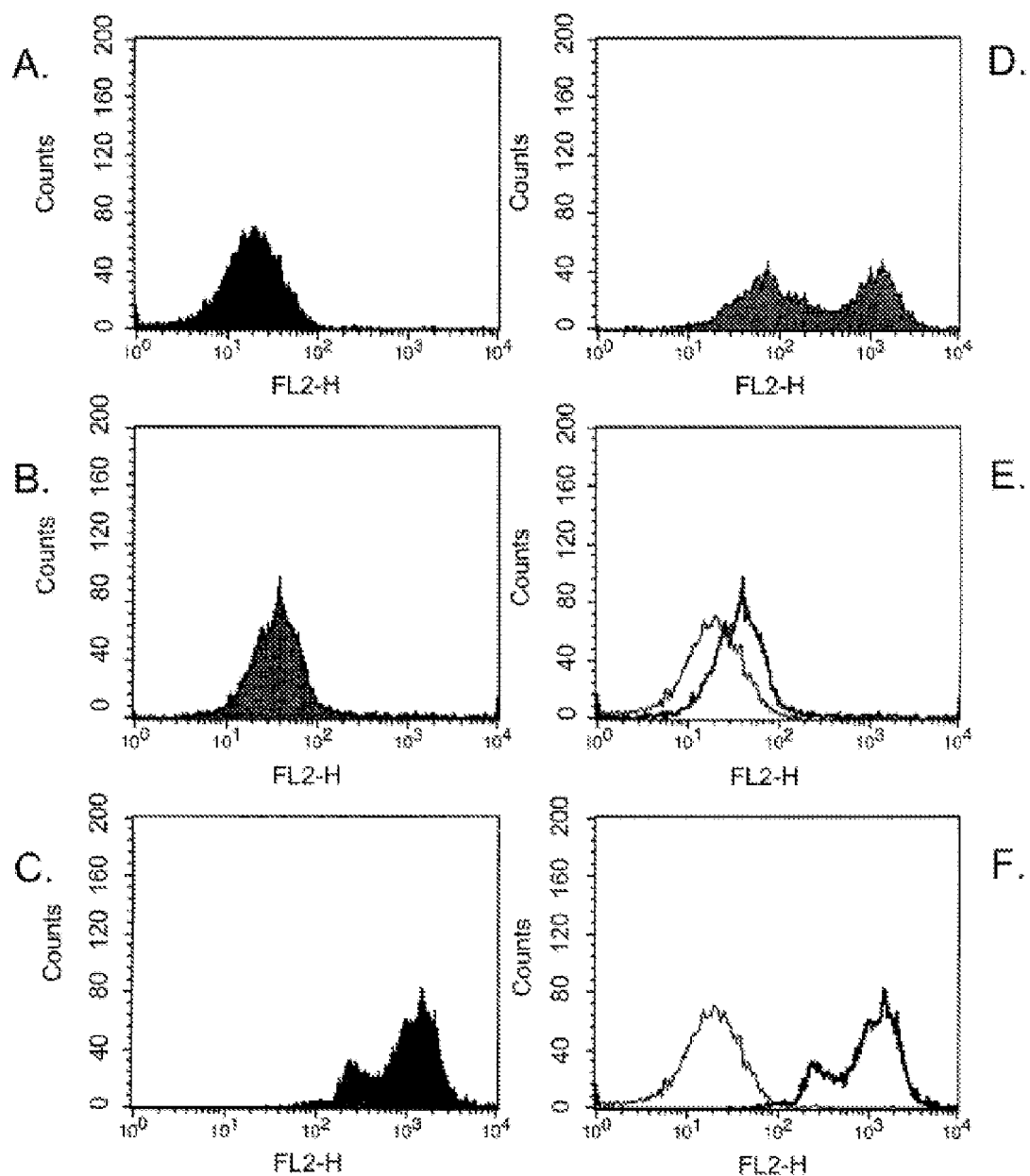
FIG. 2 shows histograms from FACS staining and sorting of neural stem cells.

FIG. 2 shows histograms from FACS staining and sorting of neural stem cells. FIG. 2A shows control where no compound is added.

FIG. 2B shows staining with Compound 1 (not binding to neural stem cells or neural cancer stem cells, Stalker 2).

FIG. 2C shows binding of Compound 2 (p-HTMI, Stalker 1) to neural stem cells.

FIG. 2D shows staining of a mixture of Compound 1 and Compound 2 to neural stem cells, showing strong binding of compound 2 as the most right hand peak to said cells.

FIG. 2E shows overlay histograms of control and compound 1 (not binding to neural stem cells) and, FIG. 2F shows overlay histograms of compound 2 (binding to neural stem cells, right hand peak) and control in left hand peak.

Example 9

Synthesis of Oligothiophene Derivative p-HTMI

Below is shown an overview of the synthesis reaction, step 1-5 generating P1 (p-HTMI).

Synthesis of 1

2-(3-thienyl)ethanol (4.00 g, 31.20 mmol) was dissolved in $CHCl_3/AcOH$ (1:1, 90 ml) and cooled to 0° C.

N-iodosuccinimide (7.37 g, 32.76 mmol) was added to the mixture and after two hours more N-iodosuccinimide (1.4 g, 6.22 mmol) was added.

After one hour the mixture was diluted with water (250 ml) and the organic phase was washed with 10%-sodium sulphate (2×70 ml) and water (2×70 ml).

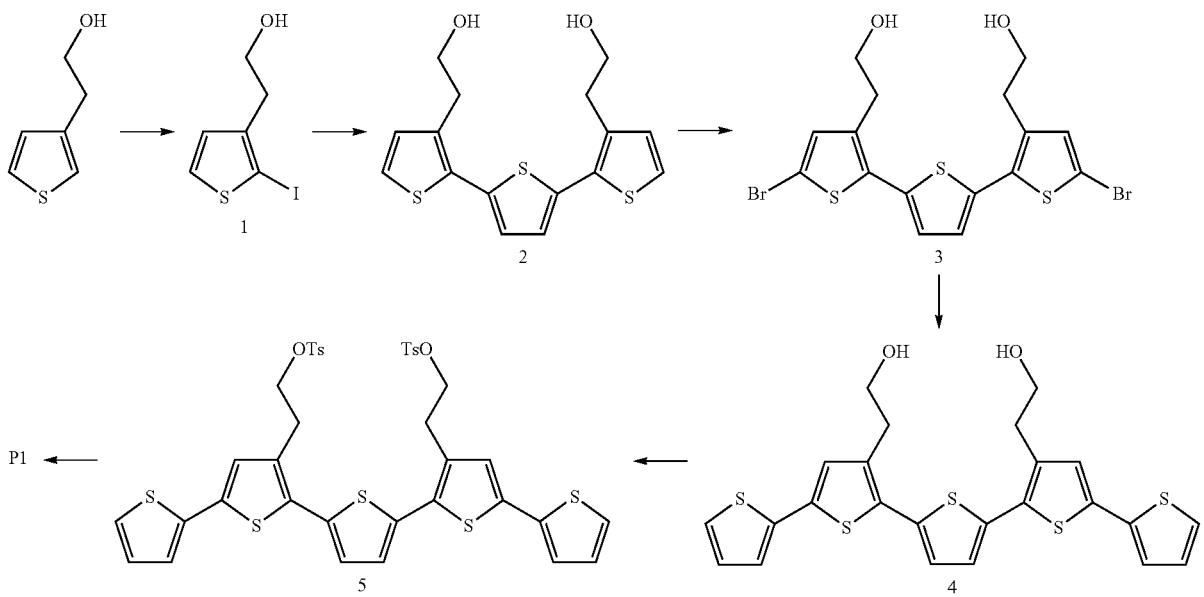

General Method

Solvents and reagents were used as supplied from the chemical supplier (Sigma Aldrich Co, Merck Sharp & Dohme Co or Frontier Scientific Co). Organic extracts were dried over anhydrous magnesium sulfate, filtered and concentrated in vacuo at 40° C. 3-thiopheneacetic acid, 2-thiopheneboronic acid and PEPPSI™-IPr ([1,3-Bis(2,6-Diisopropylphenyl)imidazol-2-ylidene](3-chloropyridyl)palladium(II) dichloride) are commercially available from Sigma-Aldrich Co. 5-(dihydroxyboryl)-2-thiophenecarboxylic acid was acquired from MAYBRIDGE®. Microwave reactions were carried out on a SmithCreator 482 microwave reactor. NMR-spectra were recorded on a Varian 300 MHz instrument. Chemical shift were assigned with the solvent residual peak as a reference according to Gottlieb et al. 1 TLC was carried out on Merck precoated 60 F254 plates using UV-light (I=254 nm and 366 nm) and charring with ethanol/sulfuric acid/panisaldehyde/acetic acid 90:3:2:1 for visualization. Flash column chromatography (FC) was performed using silica gel 60 (0.040-0.063 mm, Merck). Gradient HPLC-MS were performed on a Gilson system (Column: Phenomenex C-18 250×15 mm and Phenomenex C-18 150×4.6 mm for preparative and analytical runs respectively; Pump: Gilson gradient pump 322; UV/VIS-detector: Gilson 155; MS detector: Thermo Finnigan Surveyor MSQ; Gilson Fraction Collector FC204) using acetonitrile with 0.1% formic acid and deionized water with 0.1% formic acid as mobile phase. MALDI-TOF MS were recorded in linear positive mode with a-cyano-4-hydroxycinnamic acid matrix (CHCA) or 2,5-dihydroxy benzoic acid (DHB) as matrix.

Flush column chromatography (toluene/DCM) gave product 2 (2.08 g, 8.19 mmol).

TLC (Toluene/ethylacetat 4:1) $R_f$=0.37.

$^1$H NMR ($CDCl_3$ δ: 1.45 (t, 2H), 3.80 (t, 2H), 6.78 (d, 1H J=6 Hz), 7.46 (d, 1H, J=6 Hz)

$^{13}$C NMR ($CDCl_3$) δ: 35.5, 62.5, 75.6, 128.5, 131.0, 143.3,

Synthesis of 2

1 from the above step (0.050 g, 0.197 mmol), 2"-(2,5-thiophene)bis[4,4,5,5-tetramethyl-1,3,2-dioxaborolane] (0.034 g, 0.101 mmol) and a $K_2CO_3$ (0.024 g, 0.172 mmol) were dissolved in solvent (2 ml) under argon atmosphere.

After 10 minutes peppsi (0.004 g, 0.001 mmol) was added to the mixture and the solution were bubbled in argon for 5 minutes.

The mixture was microwave irradiated at 80° C. for 10 min.

The product was filtered, evaporated and dissolved in methanol before purified on flush column (toluene/ethylacetate 1:1) and gave product 2 (0.165 g, 0.491 mmol).

TLC (toluene/ethylacetate 2:1) $R_f$=0.17.

Synthesis of 3

Product 2 ((0.816 g, 2.42 mmol) was dissolved in $CHCl_3$/acetic acid (30 mL, 1/1) and cooled to 0° C.

N-bromosuccinimide (0.906 g, 5.10 mmol) was added.

After 1 day the reaction is purified by flush column chromatography (toluene/ethylacetate 18:1 to 4:1) and HPLC (acetonitrile/$H_2O$ 7:1 to 8:1 over 10 min) to give the product 3 (0.448 g, 37%).

Synthesis of 4

Product 3 (0.052 g, 0.105 mmol), 2-Thopheneboronic acid pinacol ester (0.066 g, 0.314 mmol), $K_2CO_3$ (0.087 g, 0.630 mmol) and PEPPSI-IPr (0.001 g, 0.0014 mmol) were added to degassed toluene/methanol (1:1, 1 mL) and microwave irradiated for 10 min at 80° C.

The solution was filtered and diluted with ethylacetate before it was washed with HCl (1M, aq), brine, and H$_2$O.

Flush chromatography gave the product in 93% yield (0.049 g).

Synthesis of 5

Product 4 (0.049 g, 0.0979 mmol) was added to CHCl$_3$ (0.8 mL) and pyridine (0.2 mL).

p-toluene sulphonyl chloride (0.056 g, 0.294 mmol).

After 4 h the solution was diluted with toluene and washed with HCl (1M, aq and H$_2$O.

Flush column chromatography (toluene) gave the product 5 in 84% yield (0.066 g).

Synthesis of P1

Product 5 (0.010 g, 0.0124 mmol) and methylimidazole (0.030 mL, 0.376 mmol) was dissolved in acetonitrile (1 mL).

After one day the mixture was concentrated to give P1 (3 mg) in 39% yield.

LC-MS calculated for C$_{32}$H$_{30}$N$_4$S$_5$: [M]$^{2+}$: 315.05; Found 315.10

The invention claimed is:

1. An oligothiophene derivate according to formula (I)

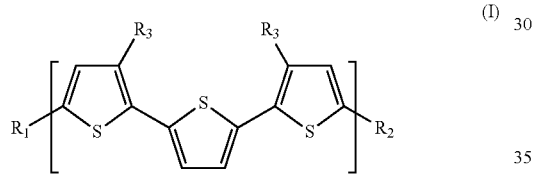
(I)

wherein
R$_3$ is chosen from

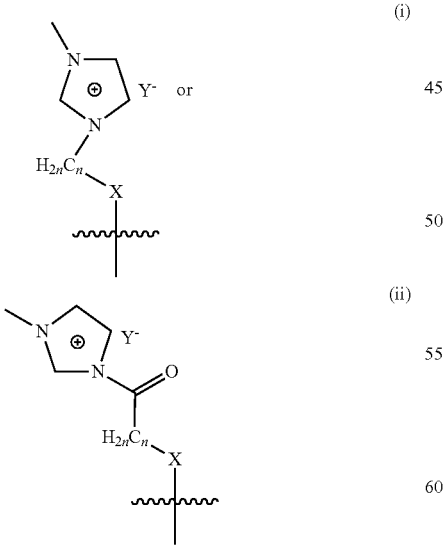

and wherein
n is selected from the group consisting of 0, 1, 2, and 3,
Y— is an anionic counter ion,
X is CH$_2$ when n=0, and X is selected from the group consisting of O and CH$_2$ when n is 1, 2, or 3, and
each R$_1$ and R$_2$ are independently selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with isotopically enriched carbon $^{11}$C (12) according to the formulas

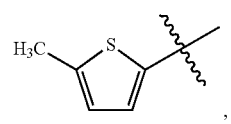
4

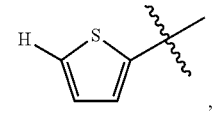
5

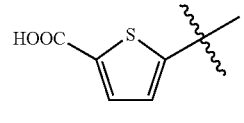
6

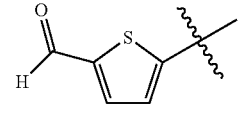
7

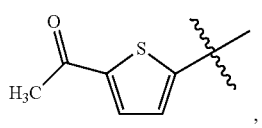
8

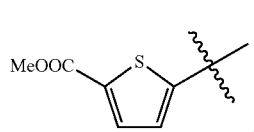
9

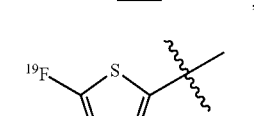
10

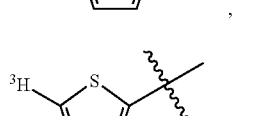
11 and

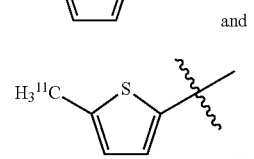
12

.

2. An oligothiophene derivate according to formula I,

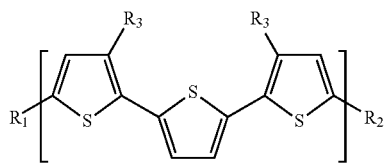
(I)

wherein $R_1$ is

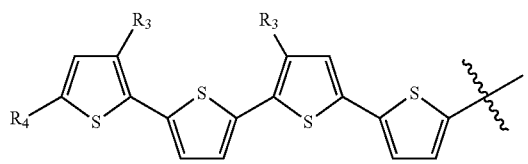
(iii)

$R_3$ is chosen from

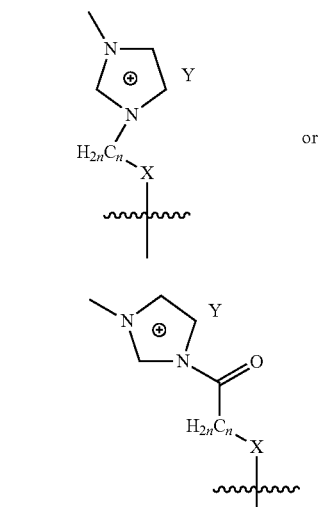
(i) or (ii)

and wherein, n is selected from the group consisting of 0, 1, 2, and 3,

Y— is an anionic counter ion,

X is $CH_2$ when n=0, and X is selected from the group consisting of O and $CH_2$ when n is 1, 2, or 3, and $R_2$ is selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}F$ or $^{19}F$ (10), 5-thiophene-2-yl with tritium (11) and 5-methylthiophene-2-yl with isotopically enriched $^{11}C$ (12) according to the formulas

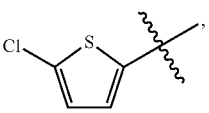
1

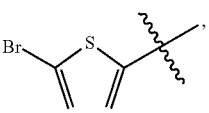
2

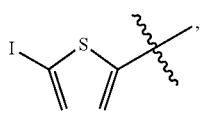
3

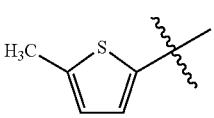
4

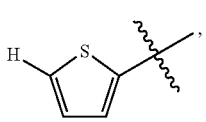
5

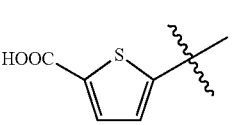
6

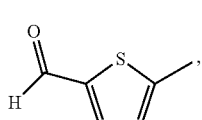
7

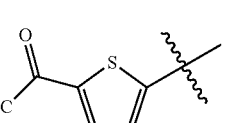
8

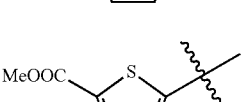
9

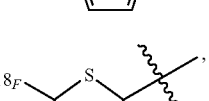
10

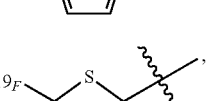
10

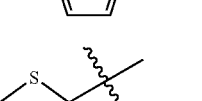
11 and

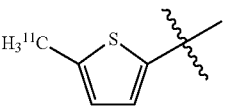
12 and wherein

R₄ is selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with isotopically enriched carbon $^{11}$C (12) according to the formulas:

4
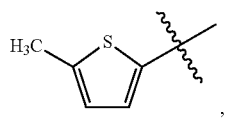,

5
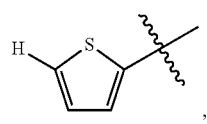,

6
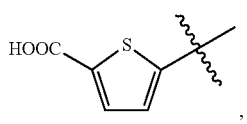,

7
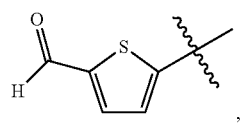,

8
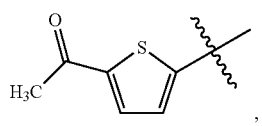,

9
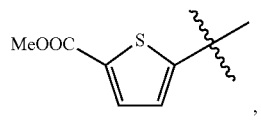,

10
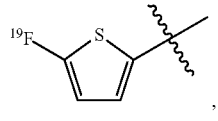,

11
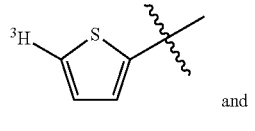

and

12
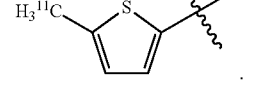.

3. An oligothiophene derivate according to formula (I),

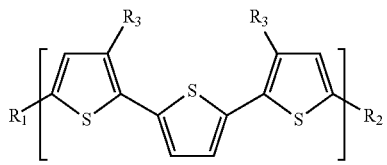

(I)

wherein R₁ is

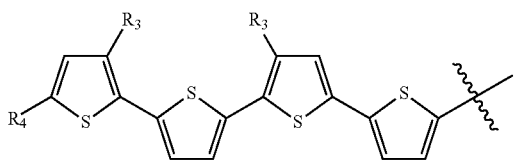

(iii)

R₃ is chosen from

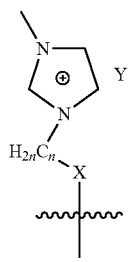

(i)

or

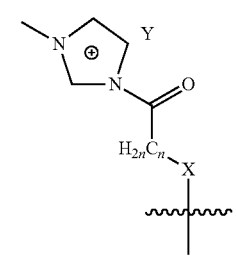

(ii)

and wherein n is selected from the group consisting of 0, 1, 2, and 3,

Y— is an anionic counter ion,

X is CH₂ when n=0, and X is selected from the group consisting of O and CH₂ when n is 1, 2, or 3, and wherein R₂ and R₄ are independently selected from the group consisting of bromine, chlorine, hydrogen, iodine, methyl, 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-5-carboxylate (9), 5-fluorothiophene-2-yl with enriched isotopes of $^{18}$F or $^{19}$F (10), 5-thiophene-2-yl with tritium (11) and 5-methylthiophene-2-yl with isotopically enriched carbon $^{11}$C (12) according to the formulas:

4
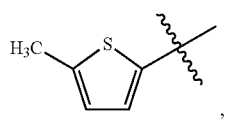
,
5
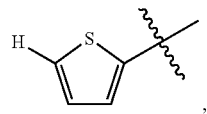
,
6
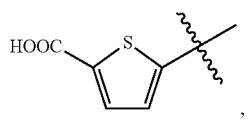
,
7
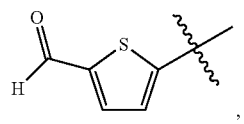
,
8
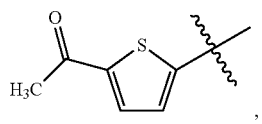
,
9
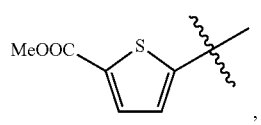
,
10
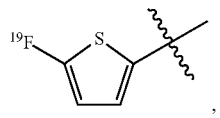
,
11
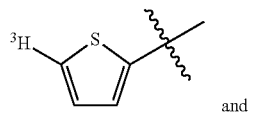
and
12
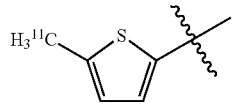
.
4. The oligothiophene derivate according to claim 1, wherein
  $R_3$ is according to formula (I),
and wherein
  n is 1,
  X is $CH_2$,
  Y— is 4-methylbenzenesulfonate, and
  $R_1$ and $R_2$ are according to formula 5 in claim 1
which will give formula
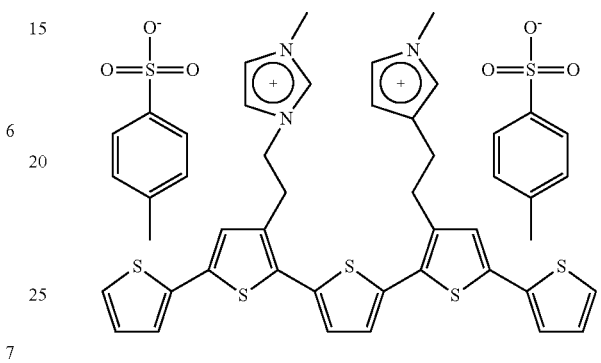
P1 (p-HTML).
5. An oligothiophene derivate according to formula (I),
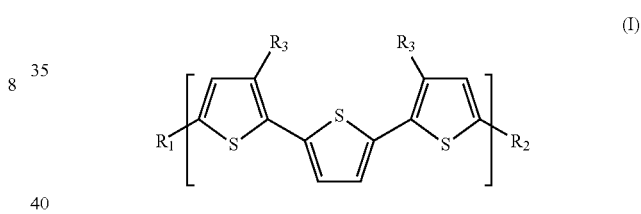
(I)
wherein $R_1$ is
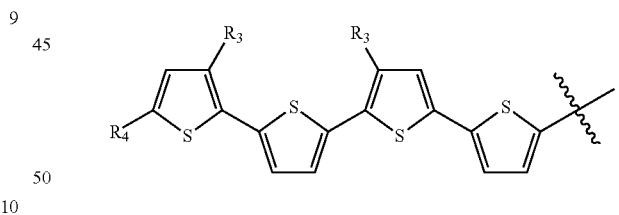
wherein $R_3$ is
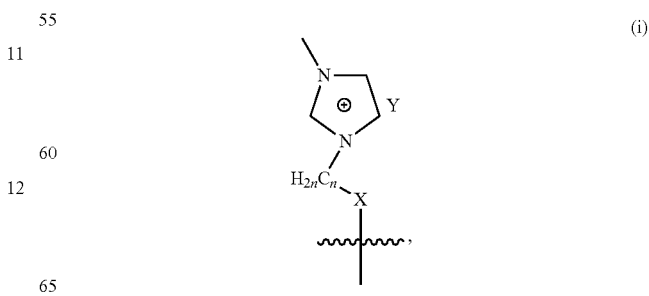
(i)

and wherein
n is 1,
X is CH$_2$,
Y— is 4-methylbenzenesulfonate,
R$_4$ is H
and
R$_2$ is hydrogen,
which will give the formula

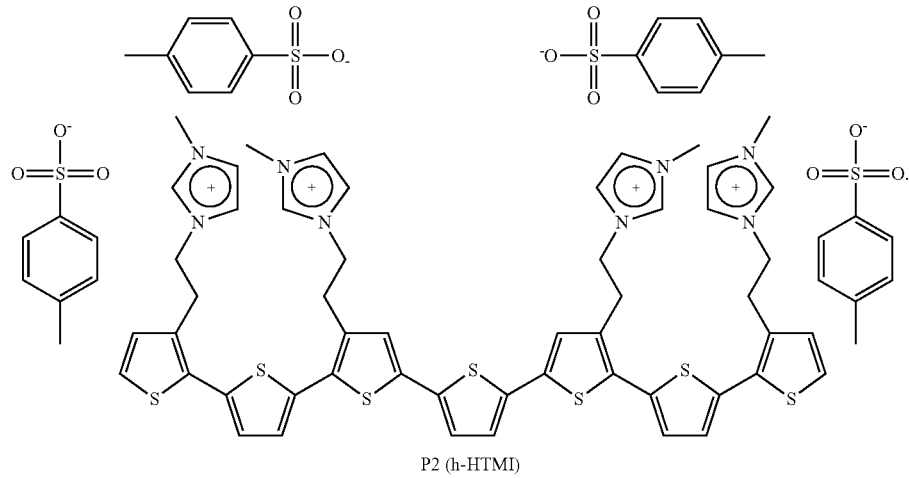

P2 (h-HTMI)

6. An oligothiophene derivate conjugated to a detectable moiety, the oligothiophene derivate according to formula (I)

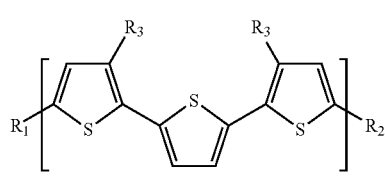

wherein
R$_3$ is chosen from

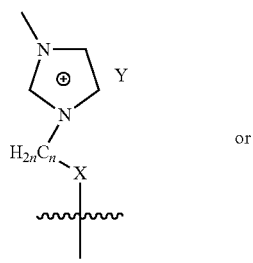

or

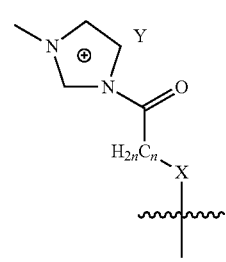

and wherein
n is selected from the group consisting of 0, 1, 2, and 3,
Y— is an anionic counter ion,
X is CH$_2$ when n=0, and X is selected from the group consisting of O and CH$_2$ when n is 1, 2, or 3, and
each R$_1$ and R$_2$ are independently selected from the group consisting of 5-chlorothiophene-2-yl (1), 5-bromothiophene-2-yl (2), 5-iodothiophene-2-yl (3), 5-methylthiophene-2-yl (4), thiophene-2-yl (5), 5-thiophenecarboxylic acid-2-yl (6), 5-formylthiophene-2-yl (7), 5-acetylthiophene-2-yl (8) and methyl 2-yl-thiophene-carboxylate (9), 5-fluorothiophene-2-yl with enriched isotopes of $^{18}$F or $^{19}$F (10), 5-thiophene-2-yl with tritium (11) and 5-methylthiophene-2-yl with isotopically enriched carbon $^{11}$C (12) according to the formulas

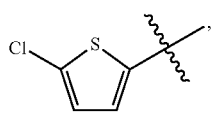
1

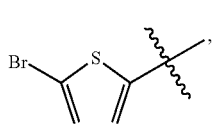
2

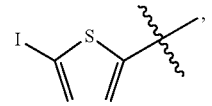
3

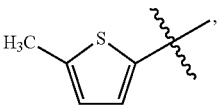
4

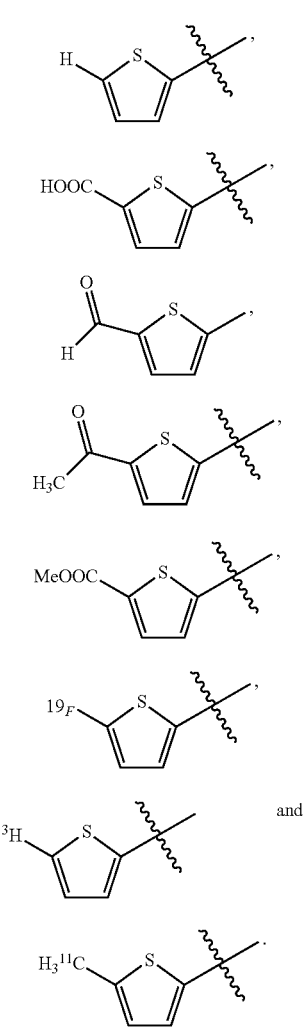

7. The oligothiophene derivate according to claim 6, wherein the detectable moiety is selected from the group consisting of a radioisotope, a radionuclide, a fluorescent label, an enzymatic label, a chemiluminescent label, a biotinyl group, a predetermined polypeptide epitope recognized by a secondary binding entity; a binding site for secondary antibody, a metal binding domain, an epitope, a protein tag, and a carbohydrate.

8. The oligothiophene derivate according to claim 7, wherein the radioisotope or radionuclide is selected from the group consisting of $^{3}H$, $^{14}C$, $^{35}S$, $^{123}I$, $^{125}I$, $^{131}I$, $^{99}Tc$, $^{111}In$, $^{90}Y$, $^{188}Re$, $^{11}C$, $^{3}H$, $^{18}F$, and $^{64}Cu$.

9. A method for detecting neural stem cells or neural cancer stem cells in a biological sample in vitro, in situ or in vivo, the method comprising the steps of
 a. contacting said sample with a composition comprising at least one oligothiophene derivate according to claim 1 to form at least one neural stern cell-oligothiophene derivate complex or to form at least one neural cancer stem cell-oligothiophene derivate complex, and
 b. detecting said neural stem cell-oligothiophene derivate complexes or neural cancer stem cell-oligothiophene derivate complexes.

10. The method according to claim 9, further comprising comparing the neural stem cell-oligothiophene derivate complexes or neural cancer stem cell-oligothiophene derivate complexes to a positive control, wherein the positive control comprises neural stem cells or neural cancer stem cells.

11. The method according to claim 9, further comprising comparing the neural stem cell-oligothiophene derivate complexes or neural cancer stem cell-oligothiophene derivate complexes to a negative control, wherein the negative control does not comprise neural stem cells or neural cancer stem cells.

12. The method according to claim 9, further comprising a step of scoring the amount of neural stem cells-oligothiophene derivate complexes or neural cancer stem celloligothiophene derivate complexes.

13. The method according to claim 9, which is performed on an automated staining device.

14. The method according to claim 9, wherein the detection is made manually.

15. The method according to claim 9, wherein the detection is made by image analysis.

16. A method for separating neural stem cells or neural cancer stem cells from other biological material in a biological sample, the method comprising the steps of
 a. contacting said sample with a composition comprising at least one oligothiophene derivate according to claim 1 to form at least one neural stem cell-oligothiophene derivate complex or at least one neural cancer stem cell-oligothiophene derivate complex,
 b. detecting said neural stem cell-oligothiophene derivate complexes or neural cancer stem cell-oligothiophene derivate complex, and
 c. separating said detected neural stem cell-oligothiophene derivate complexes or neural cancer stem cell-oligothiophene derivate complexes, thereby separating neural stem cells or neural cancer stem cells.

17. The method of claim 16, further comprising the step of isolating said neural stem cells or neural cancer stem cells.

18. The method of claim 17, wherein the isolation is done by mechanical means.

19. The method of claim 17, wherein the isolation is done by flow cytometric means.

* * * * *

UNITED STATES PATENT AND TRADEMARK OFFICE
CERTIFICATE OF CORRECTION

PATENT NO.          : 9,012,656 B2
APPLICATION NO.     : 13/577561
DATED               : April 21, 2015
INVENTOR(S)         : Hermansson et al.

Page 1 of 1

It is certified that error appears in the above-identified patent and that said Letters Patent is hereby corrected as shown below:

In the Claims

In column 56, claim 1, please insert the following after line 13:

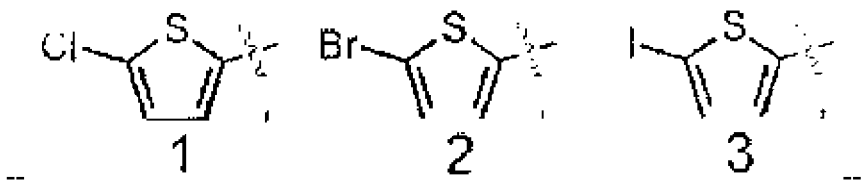

In column 66, claim 9, please change line 6 to:

form at least one neural stem cell-oligothiophene deri-

Signed and Sealed this
Nineteenth Day of January, 2016

Michelle K. Lee
*Director of the United States Patent and Trademark Office*